(12) United States Patent
Allred et al.

(10) Patent No.: US 7,192,280 B2
(45) Date of Patent: Mar. 20, 2007

(54) DENTAL BLEACHING DEVICES HAVING A PROTECTIVE ADHESIVE REGION

(75) Inventors: Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 258 days.

(21) Appl. No.: 10/783,750

(22) Filed: Feb. 19, 2004

(65) Prior Publication Data
US 2005/0186150 A1    Aug. 25, 2005

(51) Int. Cl.
*A61C 5/00* (2006.01)
*A61C 15/00* (2006.01)
*A61Q 11/00* (2006.01)
*A61K 6/00* (2006.01)

(52) U.S. Cl. .................. 433/215; 433/216; 433/217.1; 424/53; 424/401

(58) Field of Classification Search ..................... None
See application file for complete search history.

(56) References Cited

U.S. PATENT DOCUMENTS

| | | | |
|---|---|---|---|
| 165,584 A | 7/1875 | Hopfen | |
| 1,637,153 A | 7/1927 | Lawton | |
| 2,257,709 A | 9/1941 | Anderson | |
| 2,835,628 A | 5/1958 | Saffir | |
| 3,339,547 A | 9/1967 | Drabkowski | |
| 3,527,219 A | 9/1970 | Greenberg | |
| 3,577,640 A | 5/1971 | Lee ................ 32/32 |
| 3,624,909 A | 12/1971 | Greenberg | |
| 3,688,406 A | 9/1972 | Porter et al. | |
| 3,955,281 A | 5/1976 | Weitzman | |
| 4,044,762 A | 8/1977 | Jacobs ................ 128/136 |
| 4,063,552 A | 12/1977 | Going et al. ........... 128/136 |
| 4,064,628 A | 12/1977 | Weitzman | |
| 4,138,814 A | 2/1979 | Weitzman | |
| RE33,093 E | 10/1989 | Schiraldi et al. | |
| 4,900,721 A | 2/1990 | Bansemir | |
| 4,902,227 A | 2/1990 | Smith | |
| 5,008,093 A | 4/1991 | Merianos | |
| 5,051,476 A | 9/1991 | Uji et al. ................ 525/186 |
| 5,085,585 A | 2/1992 | Zimble | |
| 5,108,742 A | 4/1992 | Merianos | |
| 5,112,225 A | 5/1992 | Diesso | |
| 5,183,901 A | 2/1993 | Login et al. | |
| 5,211,559 A | 5/1993 | Hart et al. | |
| 5,310,563 A | 5/1994 | Curtis et al. | |
| 5,326,685 A | 7/1994 | Gaglio et al. | |
| 5,346,061 A | 9/1994 | Newman et al. | |
| 5,356,291 A | 10/1994 | Darnell | |
| 5,376,006 A | 12/1994 | Fischer ................ 433/215 |
| 5,425,953 A | 6/1995 | Sintov et al. | |
| 5,562,449 A | 10/1996 | Jacobs et al. | |
| 5,573,399 A | 11/1996 | McClintock, II | |
| 5,575,654 A | 11/1996 | Fontenot | |
| 5,611,687 A | 3/1997 | Wagner | |
| 5,616,027 A | 4/1997 | Jacobs et al. | |
| 5,631,000 A | 5/1997 | Pellico ................ 424/53 |
| 5,639,445 A | 6/1997 | Curtis et al. | |
| 5,702,251 A | 12/1997 | McClintock, II | |
| 5,707,235 A | 1/1998 | Knutson | |
| 5,711,935 A | 1/1998 | Hill et al. | |
| 5,752,826 A | 5/1998 | Andreiko ................ 433/41 |
| 5,769,633 A | 6/1998 | Jacobs et al. | |
| 5,816,802 A | 10/1998 | Montgomery | |
| 5,846,058 A | 12/1998 | Fischer | |
| 5,851,512 A | 12/1998 | Fischer ................ 424/49 |
| 5,863,202 A * | 1/1999 | Fontenot et al. ........ 433/215 |
| 5,879,691 A | 3/1999 | Sagel et al. | |
| 5,891,453 A | 4/1999 | Sagel et al. | |
| 5,894,017 A | 4/1999 | Sagel et al. | |
| 5,895,218 A | 4/1999 | Quinn et al. | |
| 5,922,307 A | 7/1999 | Montgomery | |
| 5,924,863 A | 7/1999 | Jacobs et al. | |
| 5,980,249 A | 11/1999 | Fontenot | |
| 5,985,249 A | 11/1999 | Fischer ................ 424/49 |
| 5,989,569 A | 11/1999 | Dirksing et al. | |
| 6,036,943 A | 3/2000 | Fischer ................ 424/49 |
| 6,045,811 A | 4/2000 | Dirksing et al. | |
| 6,080,397 A | 6/2000 | Pfirrmann | |
| 6,086,370 A * | 7/2000 | Jensen et al. ............ 433/136 |
| 6,089,869 A | 7/2000 | Schwartz | |

(Continued)

FOREIGN PATENT DOCUMENTS

| WO | WO 88/06869 | 9/1988 |
|---|---|---|
| WO | WO 99/62472 | * 12/1999 |
| WO | WO 03/000216 | 1/2003 |

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Frederick Krass
*Assistant Examiner*—Lezah Roberts
(74) *Attorney, Agent, or Firm*—Workman Nydegger

(57) ABSTRACT

Dental bleaching devices in the shape of a dental tray, strip or patch include a barrier layer, a dental bleaching composition, and a protective adhesive composition that protects a person's gums from the dental bleaching composition during use. The barrier layer protects the bleaching and protective adhesive compositions from saliva or moisture during use. The dental bleaching composition is positioned so as to contact a person's tooth surfaces when the bleaching device is in use. The protective adhesive composition is positioned so as to shield a person's gums from the bleaching composition when the bleaching device is in use. The dental bleaching composition and protective adhesive composition can be in the form of a gel or they may be substantially solid. They preferably include a tissue adhesion agent comprising a hydrophilic polymer.

35 Claims, 10 Drawing Sheets

U.S. PATENT DOCUMENTS

| | | | |
|---|---|---|---|
| 6,096,328 A * | 8/2000 | Sagel et al. | 424/401 |
| 6,106,293 A | 8/2000 | Wiesel | |
| 6,126,443 A | 10/2000 | Burgio | |
| 6,136,297 A | 10/2000 | Sagel et al. | |
| 6,142,780 A | 11/2000 | Burgio | |
| 6,155,832 A | 12/2000 | Wiesel | |
| 6,183,251 B1 | 2/2001 | Fischer | |
| 6,197,331 B1 | 3/2001 | Lerner et al. | |
| 6,247,930 B1 | 6/2001 | Chiang et al. | |
| 6,274,122 B1 | 8/2001 | McLaughlin | |
| 6,277,458 B1 | 8/2001 | Dirksing et al. | |
| 6,280,196 B1 | 8/2001 | Berghash | |
| 6,287,120 B1 | 9/2001 | Wiesel | |
| 6,306,370 B1 | 10/2001 | Jensen et al. | 424/49 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | |
| 6,331,292 B1 | 12/2001 | Montgomery | |
| 6,343,932 B1 * | 2/2002 | Wiesel | 433/215 |
| 6,364,665 B1 | 4/2002 | Trettenero | 433/215 |
| 6,379,147 B1 | 4/2002 | Georgakis et al. | 433/37 |
| 6,419,903 B1 | 7/2002 | Xu et al. | |
| 6,419,906 B1 | 7/2002 | Xu et al. | |
| 6,435,873 B1 | 8/2002 | Burgio | |
| 6,440,396 B1 | 8/2002 | McLaughlin | |
| 6,458,380 B1 | 10/2002 | Leaderman | |
| 6,461,158 B1 | 10/2002 | Sagel et al. | |
| 6,488,914 B2 | 12/2002 | Montgomery | |
| 6,497,575 B2 | 12/2002 | Zavitsanos et al. | |
| 6,500,408 B2 | 12/2002 | Chen | |
| 6,503,486 B2 | 1/2003 | Xu et al. | |
| 6,506,053 B2 | 1/2003 | Wiesel | |
| 6,514,483 B2 | 2/2003 | Xu et al. | |
| 6,514,484 B2 | 2/2003 | Rajaiah et al. | |
| 6,551,579 B2 | 4/2003 | Sagel et al. | |
| 6,649,147 B1 | 11/2003 | Ye et al. | |
| 6,682,721 B2 | 1/2004 | Kim et al. | |
| 6,689,344 B2 | 2/2004 | Chang et al. | |
| 6,730,316 B2 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagel et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

* cited by examiner

DENTAL BLEACHING DEVICES HAVING A PROTECTIVE ADHESIVE REGION

BACKGROUND OF THE INVENTION

1. The Field of the Invention

This invention is in the field of dental bleaching compositions and devices used to bleach a person's teeth. More particularly, the invention relates to bleaching compositions and devices that include a dental bleaching composition, a moisture-resistant barrier layer, and a protective adhesive region that shields soft oral tissue from the bleaching composition.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another bleaching method involves painting a bleaching composition directly onto a person's teeth. A perceived advantage of paint-on bleaching is that it eliminates the need for a dental tray. The main disadvantage of a paint-on bleaching composition is that it remains directly exposed to the person's saliva and disruptive forces found in a person's mouth. As a result, a significant portion of the bleaching composition does not remain on the teeth where bleaching is desired. Some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a plastic barrier that, at least in theory, keeps the dental bleaching gel from diffusing into the user's mouth.

In reality, because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk or smile while properly maintaining the bleaching strip in the correct position.

Even if a user successfully maintains a conventional bleaching strip in its proper position during the recommended bleaching period, the bleaching gel often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In practical terms, the use of conventional bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are the least prone to move is at night while the person is sleeping. Unfortunately, it is recommended that conventional bleaching strips not be used while sleeping, presumably to prevent accidental choking on an inadvertently dislodged bleaching strip. This confirms the tendency of conventional bleaching strips to easily dislodge from a user's teeth.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

In view of the foregoing, there is an ongoing need for improved bleaching apparatus and methods that are simple and easy to use and that reliably remain in position over the user's teeth so as to reduce diffusion of bleaching composition into a user's oral cavity. Such improvements would be expected to improve or encourage compliance by the user.

BRIEF SUMMARY OF THE PREFERRED EMBODIMENTS

The present invention relates to dental bleaching devices used to bleach a person's teeth that include a barrier layer, a dental bleaching composition positioned so as to contact a person's tooth surfaces, and a protective adhesive composition positioned so as to protect a person's gums from the bleaching composition during use. The barrier layer protects the bleaching and protective adhesive compositions from saliva and moisture during use, which keeps them in contact with a person's teeth and/or surrounding soft tissue and helps prevent, minimize or lessen their diffusion into the user's mouth.

The barrier layer is advantageously formed from a moisture-resistant polymer material, examples of which include polyolefins, polyesters, ethylene-vinyl acetate copolymer (EVA), polyurethane, other polymers, and blends thereof. It may be in the form of a dental tray, strip, patch or other desired shape. The barrier layer is advantageously thin and flexible so as to conform to the shape of a person's teeth as a result of the adhesive nature of the bleaching and protective adhesive compositions. The barrier layer may be sufficiently sturdy as to assume a particular shape prior to use, or it may be so thin and flexible as to only be capable of assuming the shape of an internal support (e.g., the shape of a substantially solid bleaching composition and/or protective adhesive composition) and/or an external support (e.g., an exoskeleton, such as an external support tray). In one embodiment, the barrier layer is reliably held in place over a user's teeth for a desired period of time by the adhesive action of the bleaching composition and/or protective adhesive composition.

The dental bleaching composition may comprise a bead, a continuous layer, or a plurality of discontinuous regions or islands. The dental bleaching composition may be in the form of a flowable bleaching gel, or it may be substantially solid. Although flowable dental bleaching compositions used in making dental bleaching devices according to the invention can have any desired viscosity and/or stickiness, bleaching gels are preferably thick and sticky so as to act as a highly viscous glue or adhesive that helps reliably maintain both the bleaching composition and barrier layer against the person's tooth surfaces to be bleached. Examples of "substantially solid" bleaching compositions are those that are initially solid or that have the consistency of a highly viscous putty prior to use. Dental bleaching compositions, particularly those that are substantially solid, can be formulated so as to become more adhesive to teeth when moistened with saliva or water during use.

Dental bleaching compositions according to the invention generally comprise a dental bleaching agent, a tissue adhesion agent, a liquid or gel solvent or carrier, and other active agents, inert ingredients or adjuvents as desired. Whether the dental bleaching composition is in the form of a gel or is substantially solid largely depends on the relative concentrations of the tissue adhesion agent and the solvent or carrier. Increasing the ratio of solvent or carrier relative to the tissue adhesion agent generally decreases the viscosity of the composition, while decreasing the ratio of solvent or carrier relative to the tissue adhesion agent yields a bleaching composition having a greater viscosity. Decreasing the concentration of the solvent or carrier at some point yields a composition that is so viscous as to be considered to be "substantially solid". In one embodiment, substantially solid bleaching compositions are manufactured by first forming a bleaching gel having a substantial quantity of a solvent and then removing some or all of the solvent by evaporation to yield a substantially solid composition. Some residual water or solvent may remain after removal of the solvent by evaporation.

Protective adhesive compositions according to the invention may comprise a gel or a substantially solid composition. They may comprise a bead, a continuous layer, or a plurality of discontinuous regions or islands. The protective adhesive composition can be formulated so as to be more viscous or less viscous than the dental bleaching composition. Like the dental bleaching composition, it can be a gel or it can be substantially solid (e.g., a true solid or a highly viscous putty). In one embodiment, it becomes more adhesive to teeth and/or soft oral tissue when moistened with saliva or water. The protective adhesive composition may include one or more active agents, inert components, and adjuvants as desired.

The main feature that distinguishes the protective adhesive composition from the dental bleaching composition is that it either includes no dental bleaching agent or a reduced amount of bleaching agent compared to the bleaching composition. Including none or a reduced quantity of bleaching agent results in a protective adhesive composition that is gentler on soft tissues compared to the dental bleaching composition. This allows the dental bleaching devices according to the invention to provide any desired concentration of bleaching agent against the tooth surfaces to be bleached while also protecting surrounding soft tissue from the potentially harsh effects of the bleaching agent.

The size and shape of dental bleaching devices according to the invention can be tailored to more readily fit a person's upper or lower dental arch. They may also be tailored to fit persons having differently-sized or shaped dental arches. In one embodiment, the dental bleaching devices are designed so as to substantially cover the front and lingual surfaces of the teeth to be bleached. Bleaching both surfaces yields more esthetically appealing teeth and helps in bleaching the interproximal spaces between adjacent teeth. The dental bleaching devices are advantageously flexible and adhesive so as to readily conform to a wide variety of differently-sized teeth and dental arches.

In one embodiment, the dental bleaching devices according to the invention are in the shape of a dental tray having a front side wall, a rear side wall, and a trough between the front and rear side walls. This facilitates placement of the dental bleaching composition or device over a person's teeth by minimizing the amount of manipulation necessary to obtain a good fit between the bleaching device and the person's teeth. In another embodiment, the dental bleaching devices are in the shape of substantially flat strips or patches prior to use. Regardless of their initial shape, the inventive dental bleaching compositions and devices are designed to more reliably remain in place over the person's teeth compared to conventional bleaching strips. The result is more effective tooth bleaching and better patient compliance.

The dental bleaching compositions and devices according to the invention can be designed to be worn for any desired time period. In general, increasing the concentration of dental bleaching agent within the bleaching composition reduces the time required to effect tooth bleaching. Nevertheless, due to the comfortable fit and reliable adhesion between the inventive dental bleaching devices and the person's teeth, it is possible to wear such devices for extended periods of time to ensure even and thorough bleaching. Dental bleaching devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The dental bleaching devices can be designed to be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours. Bleaching sessions may be repeated as many times as are needed to obtain a desired degree of whitening. In some cases, a clinical whitening effect can be observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple dental bleaching devices may be packaged together and sold as a kit. In one embodiment, the number of dental bleaching devices provided with each kit can equal the number of sessions that represent a prescribed bleaching regimen. To efficiently utilize the space within a kit package, multiple dental bleaching devices can be stacked, internested, or laid together within a package. The dental bleaching devices can be sealed collectively or individually as desired. They may contain a removable protective layer on their interior surfaces to protect the bleaching composition from contamination or moisture, both of which can possibly cause decomposition of certain bleaching agents.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
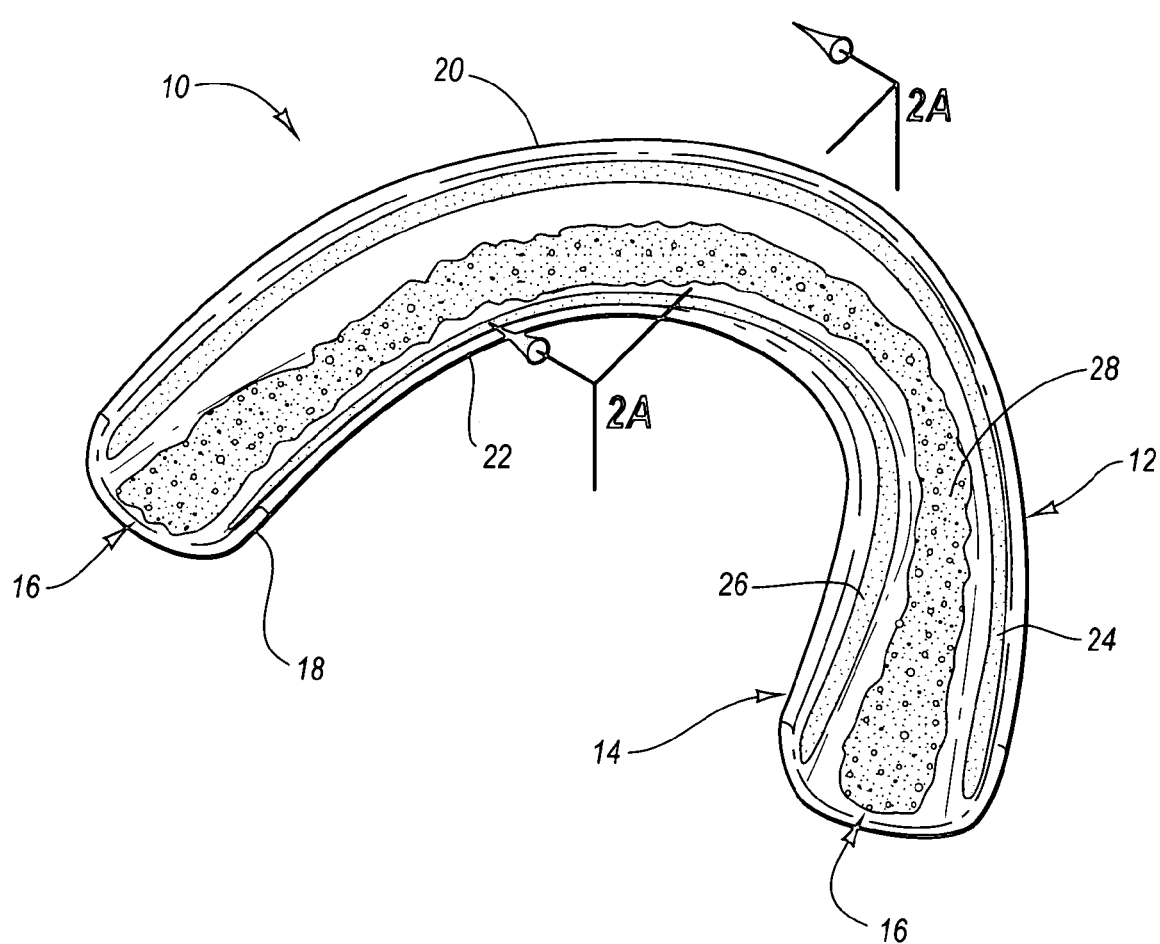
FIG. 1 is a perspective view of an exemplary dental bleaching device according to the invention in the shape of a dental tray comprising a barrier layer, a dental bleaching composition, and a protective adhesive composition nearer the front and back rims.

The present invention relates to improved dental bleaching devices used to bleach a person's teeth. The inventive dental bleaching devices include a moisture-resistant barrier layer, a dental bleaching composition positioned so as to contact a person's tooth surfaces, and a protective adhesive composition positioned so as to protect a person's gums from the bleaching composition during use. The barrier layer protects the bleaching composition and protective adhesive composition from saliva or moisture within a person's mouth during use, which keeps them in contact with the person's teeth and/or surrounding soft tissue and helps prevent or minimize their diffusion into the user's oral cavity.

The inventive bleaching devices are more adhesive to teeth than conventional dental bleaching strips and are less intrusive than bulky, over-the-counter, non-custom or boil-and-bite dental trays. In some cases they may be as reliable as, or even more reliable than, custom-fitted dental trays in maintaining a dental bleaching composition against a person's teeth. To some people they may be at least as comfortable as custom-fitted trays.

The term "barrier layer", as used herein, refers to one or more layers of a material that protects the bleaching composition and protective adhesive composition from ambient moisture and saliva found within a person's mouth when the dental bleaching device is placed over the person's teeth. The barrier layer may also serve to protect the bleaching and adhesive compositions from moisture and contaminants during storage and prior to use. The barrier layer may be in any desired form including, but not limited to, a dental tray, a tray-like shape, a strip or a patch. The terms "strip" and "patch" are essentially synonymous and refer to barrier layers and bleaching devices that are essentially flat or formless prior to placing the bleaching device over a person's teeth.

The term "gel" shall refer to bleaching and/or adhesive compositions that have been formulated or processed so as to be flowable, either by the force of gravity (i.e., having no yield stress) or that do not flow by the force of gravity but which are viscous or plastic such that they can be shaped or manipulated (e.g., they can be expressed from a syringe orifice or other dispensing means known in the art). The term "gel" broadly encompasses a wide range of compositions having greatly varying viscosities, although bleaching and protective adhesive gels according to the invention are preferably sufficiently thick or viscous that they will not run out or off of a dental tray, tray-like device or other barrier layer by gravity alone. In one embodiment, the bleaching and/or adhesive gel may be rubbery or highly viscous. At some point, when the viscosity becomes so great as to yield a composition that is substantially solid (e.g., a stiff or highly viscous putty), the composition may be considered to be "substantially solid".

The term "substantially solid", as used herein, refers to a bleaching composition or protective adhesive composition or region that is in a solid or semi-solid condition. In one aspect, a "substantially solid" composition or region can be characterized as a cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of a bleaching composition or protective adhesive composition, also excludes dry particulate compositions or powders because dry particulates and powders readily flow when subjected to gravity and/or are readily separated (i.e., the particles as a whole have little or no internal cohesion). Moreover, powders or particulates, when viewed as a whole, are not coherent or solid.

In one embodiment, the "substantially solid" compositions or regions become more adhesive when moistened with saliva or water. When moistened, the surface of the substantially solid composition or region turns into a sticky material that is able to more strongly adhere to teeth compared to a substantially solid composition or region that has not been moistened. The substantially solid composition may, at least on the surface, become a viscous liquid, paste or gel, at least temporarily, depending on the amount of moisture that is applied to the surface of the "substantially solid" composition or region. The consistency of the moistened surface can remain "substantially solid" depending on the degree of initial moistening, or it can stiffen and even revert back to being "substantially solid" as the initial quantity of surface moisture diffuses into a remaining portion of the "substantially solid" composition or region over time (e.g., during a bleaching procedure in which the composition is protected from saliva and ambient moisture in a person's mouth by a moisture-resistant barrier layer).

The term "dental tray", as used herein, refers to a bleaching device having a tray-like shape so as to facilitate placement of the device over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition portion, configured to engage lingual surfaces of the person's teeth, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case where the front and rear side walls are connected by a transition portion (e.g., a trough having a U-shaped or rectangular cross section), at least a portion of the front and rear side walls may be substantially parallel (i.e., be offset by an angle of approximately 0°) or offset by a very small angle. In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls may be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when referring to a dental tray or treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The terms "strip" or "patch" are used interchangeably and shall refer to any barrier layer or bleaching device that is substantially flat, or that only has a slight curvature or bend but that does not constitute a "dental tray", as that term is understood in the art. A "strip" or "patch", includes an inner surface or region generally oriented toward the front and/or rear surfaces of a person's teeth and/or gums when in use and an outer surface that is generally oriented away from the person's teeth and/or gums. A "strip" or "patch" may be configured so that a portion of the inner surface is oriented toward the incisal or occlusal edges of the person's teeth during use. The strip or patch may be curved or straight in one or both of the lengthwise and widthwise directions in order to fit over a user's teeth and/or gums in a desired manner.

The term "molecular weight", as used herein, shall refer to number average molecular weight expressed in Daltons, unless otherwise specified.

II. Dental Bleaching Devices

Dental bleaching devices according to the invention include a barrier layer that protects a dental bleaching composition and a protective adhesive composition from ambient moisture within a person's mouth during use. In one embodiment, the dental bleaching composition is positioned adjacent to the barrier layer in a manner so as to contact one or both tooth surfaces to be bleached, and the protective adhesive composition is positioned adjacent to the barrier layer nearest the rim or edges of a bleaching tray or strip so as to form a barrier or region that shields a person's gums from the bleaching composition. One or both of the bleaching and protective compositions can be in gel form, or they can be substantially solid. Following are preferred examples of barrier layers, bleaching compositions, and protective adhesive compositions according to the invention, as well as characteristics of bleaching devices made therefrom.

A. Barrier Layers

The barrier layer can have any desired shape or thickness. It is preferably moisture-resistant in order to protect the bleaching and protective adhesive compositions from ambient moisture found in a person's mouth. According to one embodiment, the barrier layer comprises a thin, flexible membrane formed from a moisture-resistant polymer material. The barrier layer may comprise a conventional dental tray, examples of which include both customized and non-custom dental trays, or it may initially be a strip or patch, or have some other configuration.

Examples of materials that can be used to form the barrier layer include, but are not limited to, polyolefins, wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Examples of suitable polyolefins that can be uses to make the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and polypropylene (PP), preferably comprising about 5% to about 35% PP, more preferably about 10% to about 30% PP, more especially preferably about 15% to about 25% PP, and most preferably about 20% PP, with the balance comprising ethylene-vinyl acetate (EVA), and optionally other polymers and/or small quantities of additives such as plasticizers.

Other materials that can act as a barrier layer include cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like.

In general, the thickness of the barrier layer can be selected to yield a dental bleaching device having a desired level of strength, rigidity, resilience, and flexibility. In order for the barrier layer to be sufficiently flexible so as to conform to a person's teeth as result of adhesive action by the bleaching composition and/or protective adhesive composition, the barrier layer will preferably have a thickness ranging from about 0.025 mm to about 1.5 mm, more preferably in a range of about 0.05 mm to about 1 mm, and most preferably in a range of about 0.1 mm to about 0.75 mm.

B. Dental Bleaching Compositions

The bleaching compositions within the bleaching devices according to the invention may comprise any bleaching composition known in the art. They may comprise a gel (sticky or non-sticky) or they may be substantially solid. Preferred bleaching gels are those that are substantially viscous and tacky in order to assist the protective adhesive composition in retaining the bleaching device against a person's teeth during use. Preferred bleaching compositions that are substantially solid become more adhesive to teeth when moistened with water or saliva. The bleaching compositions may comprise a continuous layer or bead positioned so as to cover a person's front tooth surfaces, rear tooth surfaces, or both, or they may comprise separate beads, layers or islands separated by one or more spaces. They can be positioned directly adjacent to the barrier layer, or at least a portion of the bleaching composition may be positioned adjacent to the protective adhesive composition.

In general, dental bleaching gels will include at least one dental bleaching agent, at least one tissue adhesion (or thickening) agent, and a liquid or gel, solvent, carrier or vehicle into which the dental bleaching agent and tissue adhesion agent are dispersed. The bleaching gel may optionally include other active agents (e.g., desensitizing agents, remineralizing agents, antimicrobial agents, and the like), as well as inert ingredients (e.g., plasticizers, humectants, neutralizing agents, thickening agents, flavorants, sweeteners, and the like).

The main difference between a bleaching composition that is a "bleaching gel" or that is "substantially solid" is the level of solvent or carrier within the composition. In general, the greater the concentration of solvent or carrier relative to the tissue adhesive agent, the less viscous the gel. The lower the concentration of solvent or carrier relative to the tissue adhesion agent, the more viscous the gel. At some point, the ratio of solvent or carrier to tissue adhesion agent is low enough so that the composition is or becomes a stiff or highly viscous putty, which may be characterized as being "substantially solid". Stiff putties preferably become more adhesive to teeth when moistened with water or saliva. Substantially solid bleaching compositions can have so little solvent or carrier as to feel dry to the touch and be initially non-adhesive but then become adhesive to teeth when moistened with water or saliva. Substantially solid bleaching compositions can be made by initially including a very small amount of solvent or carrier and/or by first forming a bleaching gel that is later dried to remove a substantial portion of the solvent or carrier.

Exemplary dental bleaching gels, and methods for making such gels, which may be used to manufacture the bleaching compositions and devices according to the invention are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat.

No. 6,500,408; and U.S. Pat. No. 6,503,485. For purposes of disclosing dental bleaching gels, and methods of making such gels, the foregoing patents are incorporated herein by reference. The bleaching gels disclosed in the foregoing patents can be converted to substantially solid bleaching compositions by substantially reducing the quantity of solvent or carrier.

Examples of substantially solid dental bleaching compositions and methods for manufacturing such compositions are disclosed in U.S. application Ser. No. 10/446,235, filed May 27, 2003; U.S. application Ser. No. 10/446,471, filed May 27, 2003; and U.S. application Ser. No. 10/646,443, filed Aug. 22, 2003. For purposes of disclosing dental bleaching compositions that are substantially solid, and methods of making such compositions, the foregoing U.S. patent applications are incorporated herein by reference.

Heating a bleaching gel to drive off water or other solvent so as to yield a substantially solid adhesive composition can destabilize the bleaching agent and render it less potent. Accordingly, it may be desirable to include one or more bleaching agent stabilizers that assist in maintaining the potency and stability of the dental bleaching agent when removing the solvent by evaporation.

Following are preferred bleaching agents, tissue adhesion agents, solvents or carriers, and other components within preferred bleaching composition used to manufacture dental bleaching devices according to the invention.

1. Bleaching Agents

Any bleaching agent capable of bleaching teeth can be used. A common dental bleaching agent that is known to bleach teeth and that has been found to be safe for oral use is hydrogen peroxide. However, hydrogen peroxide does not itself exist free in nature, but as an aqueous solution or a complex. Aqueous hydrogen peroxide is an acceptable dental bleaching agent to the extent that an anhydrous bleaching composition is not desired. Non-limiting examples of hydrogen peroxide complexes include carbamide peroxide and metal perborates (e.g., sodium perborate). Other bleaching agents that can be used to bleach teeth include, but are not limited to, metal percarbonates (e.g., sodium percarbonate), metal peroxides (e.g., calcium peroxide), metal chlorites and hypochlorites, peroxy acids (e.g., peroxyacetic acid), and peroxy acid salts.

Bleaching agents within the dental bleaching compositions according to the invention can have any desired concentration, e.g., between 1–90% by weight of the dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period. The one or more bleaching agents are preferably included in an amount in a range of about 1% to about 60% by weight of the dental bleaching composition, more preferably in a range of about 5% to about 40% by weight, and most preferably in a range of about 10% to about 30% by weight.

2. Tissue Adhesion Agents

Useful tissue adhesion agents (or tackifying agents), which can also act as thickening agents that increase the viscosity of the dental bleaching composition, include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating dental bleaching compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the dental bleaching composition is a gel, the one or more tissue adhesion agents are preferably included in an amount in a range of about 1% to about 50% by weight of the dental bleaching gel, more preferably in a range of about 3% to about 30% by weight, and most preferably in a range of about 5% to about 20% by weight.

In the case where the dental bleaching composition is substantially solid, the one or more tissue adhesion agents are preferably included in an amount in a range of about 10% to about 90% by weight of the substantially solid adhesive composition, more preferably in a range of about 20% to about 80% by weight, and most preferably in a range of about 40% to about 75% by weight.

3. Carriers and Vehicles

Dental bleaching gels for use in making dental bleaching devices according to the invention will typically include one or more liquid or gel, solvents, carriers or vehicles into which the dental bleaching agent, tissue adhesion agent, and other components are dissolved or dispersed. The solvent, carrier or vehicle will typically comprise the balance of components in the dental bleaching gel in addition to the bleaching agent, tissue adhesion agent, and other components.

Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

In the case of bleaching compositions that are substantially solid, the concentration of solvent, carrier or vehicle will typically be attenuated compared to bleaching gels. Where it is desired to form a bleaching gel that is later converted into a substantially solid bleaching composition, it may be advantageous to include one or more volatile solvents that can be removed by evaporation (e.g., water, alcohols, acetone, and other organic solvents). Because of the affinity of hydrophilic polymers for water, even bleaching compositions that appear to be solid may include a significant amount of bound water (e.g., up to about 10% or more by weight of the bleaching composition). In the case where the bleaching composition has the consistency of a highly viscous or stiff putty, the composition will generally include a solvent, carrier or vehicle that acts as a plasticizer or softening agent.

4. Other Components

The dental bleaching compositions may optionally include other active or inert components as desired to yield bleaching compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal pyrophosphates, alkyl sulfates, such as sodium lauryl sulfate, tin salts, such as sodium stannate, and tartrates), neutralizing agents (e.g., sodium hydroxide and triethanolamine), inorganic thickening agents (e.g., fumed silica), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

B. Protective Adhesive Compositions

The protective adhesive compositions used in manufacturing dental bleaching devices according to the invention are characterized as having no bleaching agent, or significantly less bleaching agent, than the dental bleaching composition. Aside from that, they may include any of the components set forth above with respect to the dental bleaching composition. The protective adhesive composition is positioned relative to the bleaching composition so as to shield a person's gums or periodontal tissue from the bleaching composition during use, thereby confining the bleaching agent within the bleaching composition to an area adjacent to the person's tooth surfaces to be bleached.

Like the bleaching composition, the protective adhesive composition can be a gel or can be substantially solid. It can be one or more continuous beads or layer, or it can comprise a plurality of discontinuous islands or regions. The protective adhesive layer can be positioned in a limited region near the rim(s) or edge(s) of the barrier layer nearest the person's gums when the bleaching device is in use, or a portion may extend beneath the bleaching composition. Alternatively, a bead of the protective adhesive composition may be positioned on top of a portion of the bleaching composition.

Examples of substantially solid adhesive compositions that can be used as a protective layer to shield a person's gums and periodontal tissue from the bleaching composition are disclosed in U.S. application Ser. No. 10/637,237, filed Aug. 8, 2003; U.S. application Ser. No. 10/646,484, filed Aug. 22, 2003; and U.S. application Ser. No. 10/646,443, filed Aug. 22, 2003. For purposes of disclosing substantially solid adhesive compositions, the foregoing applications are incorporated herein by reference. Examples of adhesive gel compositions are disclosed in U.S. Pat. No. 5,770,182; U.S. Pat. No. 5,855,870; U.S. Pat. No. 5,851,512; U.S. Pat. No. 5,5,985,249; and U.S. Pat. No. 6,036,943. For purposes of disclosing adhesive gel compositions, the foregoing patents are incorporated herein by reference.

In general, protective adhesive compositions will include at least one tissue adhesion (or tackifying) agent and a liquid or gel solvent, carrier or vehicle into which the tissue adhesion agent is dispersed, at least in the case of a gel and/or during the manufacture of a substantially solid adhesive composition. The tissue adhesion agent preferably comprises a hydrophilic polymer (e.g., one or more of the hydrophilic polymers discussed above with respect to the dental bleaching composition). The relative amount of tissue adhesion agent to liquid solvent, carrier or vehicle can be varied to yield either a gel or a substantially solid adhesive composition, as discussed above.

The solvent, carrier or vehicle may comprise any of the solvents, carriers or vehicles discussed above with respect to the bleaching composition. The amount can be varied to yield either a gel or a substantially solid adhesive composition. An adhesive gel can be heated or otherwise processed to remove a substantially quantity of solvent or carrier to yield a substantially solid adhesive composition. In one embodiment, the substantially solid protective adhesive composition is initially non-adhesive or less adhesive but becomes more adhesive to teeth and soft oral tissues when moistened with saliva or water.

In one embodiment, the protective adhesive compositions may include a dental bleaching agent in a lesser amount than the dental bleaching composition. In that way, the portion of the tooth, if any, that contacts the protective adhesive composition rather than the bleaching composition can still be subjected to tooth bleaching. In addition, peroxide bleaching agents are known to have an antimicrobial effect, thus potentially acting as a disinfecting and freshening agent to gums and periodontal tissue when included in an amount that does not cause damage to or burn such tissues. The protective adhesive compositions may include a dental bleaching agent in a range of 0% to about 10% by weight of the adhesive composition, preferably in a range of about 1% to about 10%, and more preferably in a range of about 5% to about 10% by weight.

The protective adhesive composition may include other components as desired, including colorants (e.g., carotene), gingival soothing agents (e.g., aloe vera, mild potassium nitrate, isotonic solution-forming salts (e.g., sodium chloride in an amount of about 0.9% by weight), and anesthetics (e.g., benzocaine, lidocain and the like), antioxidants (e.g., vitamin A, vitamin C, vitamin E, other vitamins, chlorophyll and carotene), flavoring agents, antimicrobial agents and preservatives (e.g., sodium benzoate, parabens, triclosan, phenols, chlorhexidine, and cetylpyridinium chloride), mouth freshening agents (e.g., camphor and wintergreen), inorganic thickening agents (e.g., fumed silica and fumed aluminum oxide), remineralizing agents (e.g., sodium fluoride or other fluoride salts), bleaching agent stabilizers, antiplaque agents, anti-tartar agents, and other adjuvents as desired.

At least a portion of the protective adhesive composition may also include one or more bleaching agent activators that are released when the bleaching device is moistened with saliva and/or mixed with the dental bleaching composition upon placing the bleaching device over the person's teeth. The adhesive compositions may comprise any known bleaching agent activator that is capable of destabilizing a dental bleaching agent in order to accelerate bleaching. When peroxides are destabilized they more rapidly release oxygen radicals, which cause tooth bleaching. The bleaching agent activator is advantageously retained within the substantially solid adhesive composition prior to use (e.g., is locked within a substantially solid or gel matrix), but which diffuses, leaches, or otherwise contacts, mixes or reacts with the bleaching composition upon moistening the bleaching and/or adhesive composition with saliva or water. In one embodiment, the bleaching composition is initially substantially anhydrous and/or does not initially touch the protective adhesive composition in order to prevent diffusion or leaching of the bleaching agent activator into the bleaching composition prior to use.

One class of bleaching agent activators includes bases (i.e., substances that raise the pH in aqueous systems). Examples of useful bases that can destabilize bleaching agents and thereby accelerate bleaching include oxides, hydroxides, carbonates, and bicarbonates of alkali metals and alkaline earth metals, and amines. Non-limiting examples include sodium oxide, sodium hydroxide, potassium oxide, potassium hydroxide, sodium carbonate, sodium bicarbonate, ammonium hydroxide, magnesium hydroxide, sodium phosphate tribasic, and ethanolamine. Bases, when used as bleaching agent activators, are preferably included in an amount in a range of about 0.1% to about 20% by weight of the adhesive composition, more preferably in a range of about 1% to about 10% by weight, and most preferably about 7% by weight.

Another class of bleaching agent activators includes metals and metal compounds. Examples of metals and metal compounds include transition metals (e.g., powders or fine particulates of iron, cobalt, nickel, copper, zinc, manganese, chromium, and the like) or metal compounds (e.g., halides or sulfates of iron, cobalt, nickel, copper, zinc, manganese, chromium, and the like). More specific examples include iron and manganese metal, manganese chloride, manganese citrate, ferrous sulfate, and manganese sulfate.

Another class of bleaching agent activator includes enzymes, particularly organo-metallic enzymes containing transition metals, such as iron. One example is "catalase", which is described more particularly in U.S. Pat. No. 6,485,709 to Banerjee et al.

Metals, metal compounds, and organo-metallic enzymes, when used as a bleaching agent activator, are preferably included in an amount in a range of about 0.01% to about 20% by weight of the adhesive composition, more preferably in a range of about 0.05% to about 10% by weight, and most preferably in a range of about 0.1% to about 5% by weight.

In one embodiment, the protective adhesive composition includes both a bleaching agent activator and bleaching agent stabilizer. Where the bleaching composition directly contacts the protective adhesive composition, the effects of the bleaching agent stabilizer may predominate prior to moistening the protective adhesive composition and/or bleaching composition with water or saliva. Thereafter, upon moistening the protective adhesive composition and/or bleaching composition with water or saliva the effects of the bleaching agent activator may predominate. Many chemical reactions, including activating a peroxide bleaching agent, have a threshold activation energy requirement. The bleaching agent stabilizer can act to raise the activation energy requirement just enough to prevent or inhibit activation of the bleaching agent prior to moistening the protective adhesive composition or bleaching composition with water or saliva but not so much as to prevent or inhibit activation after moistening occurs. This careful balance can be determined and optimized by testing protective adhesive compositions having varying concentrations of bleaching agent activator and bleaching agent stabilizer. Alternatively, the bleaching agent activator can be concentrated within the interior of the protective adhesive composition and/or the bleaching agent stabilizer can be concentrated at the surface of the protective adhesive composition.

D. Characteristics of Dental Bleaching Devices

In one embodiment, the dental bleaching devices according to the invention are in the shape of a dental tray having a front side wall, a rear side wall, and a trough between the front and rear side walls. Having the shape of a dental tray facilitates placement of the dental bleaching device over a person's teeth by reducing the amount of manipulation necessary to obtain a good fit between the device and the person's teeth. In another embodiment, the bleaching devices are in the shape of a patch or strip. It is within the scope of the invention for the bleaching devices to have any desired shape or configuration. In contrast to conventional bleaching strips, which are not recommended for use while a person eats, drinks, smokes or sleeps, dental bleaching devices according to the invention can be designed so as to be worn while talking, sleeping, eating, drinking, smiling, frowning, grimacing, yawning, coughing, smoking, or making virtually any facial expression or mouth contortion.

Figure 2A:
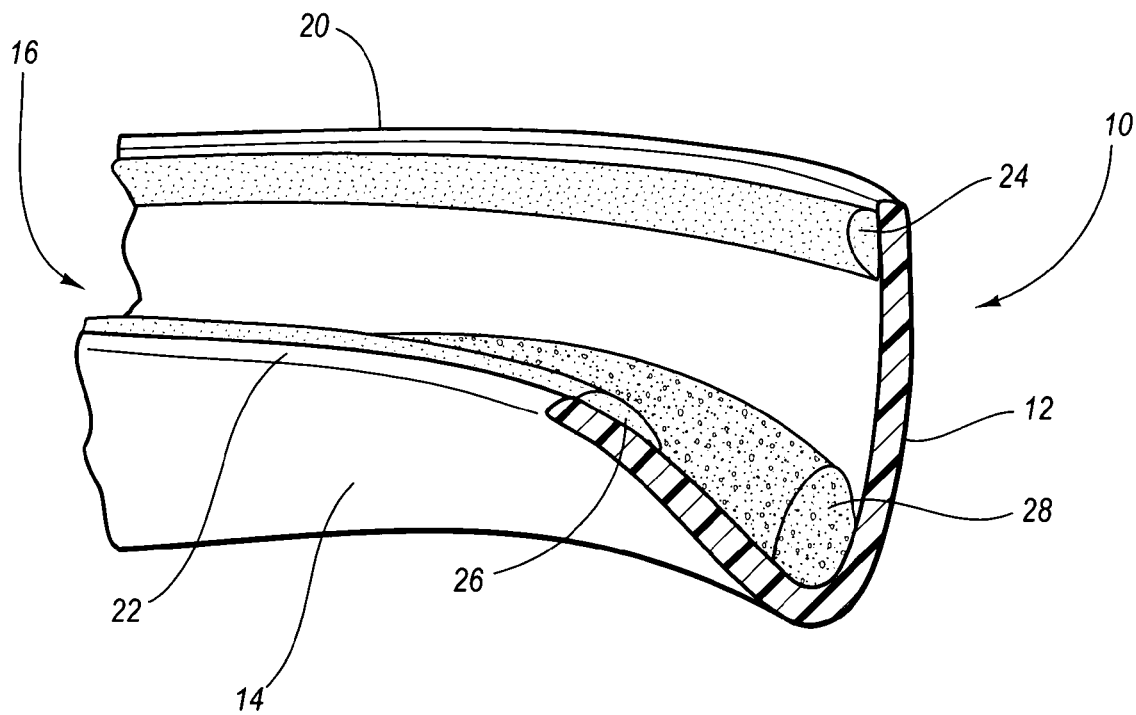
FIG. 2A is a cross-sectional view of the dental bleaching device of FIG. 1.

According to one embodiment, the dental bleaching devices have a horseshoe shaped longitudinal profile and a trough with a U-shaped cross section, much like a conventional bleaching tray. An exemplary dental bleaching device in the form of a dental tray is depicted in FIGS. 1 and 2A. FIG. 1 is a perspective view of a dental bleaching device 10 having a front side wall 12 and a rear side wall 14 that together have a generally horseshoe shape in a longitudinal dimension and that define a trough 16 having a generally U-shaped cross section. The U-shaped cross section of the trough 16 is seen more clearly in FIG. 2A.

The dental bleaching device 10 further includes a barrier layer 18, preferably comprising a moisture-resistant material, which has a front rim 20 and a back rim 22. A first protective adhesive composition or region 24 is positioned adjacent to the front rim 20 of the barrier layer 18, a second protective adhesive composition or region 26 is positioned adjacent to the back rim 22 of the barrier layer 18, and a dental bleaching composition 28 is positioned between the first and second protective adhesive compositions 24, 26. In this way, the first protective adhesive composition 24 protects the labial gums from the bleaching composition 28, and the second protective adhesive composition 26 protects the lingual gums from the bleaching composition 28, when the bleaching device 10 is placed over a person's teeth. In this way, the bleaching composition 28 is confined so as to primarily or exclusively contact the labial and lingual tooth surfaces of the teeth to be bleached.

In one embodiment, one or both of the front and back rims 20, 22 of the barrier layer are designed so as to terminate at or shy of the gingival margin when the dental bleaching device 10 is in use. In another embodiment, one or both of the front and back rims 20, 22 of the barrier layer are designed so as to extend beyond the gingival margin and partially overlap the person's gums when the dental bleaching device 10 is in use.

Figure 2B:
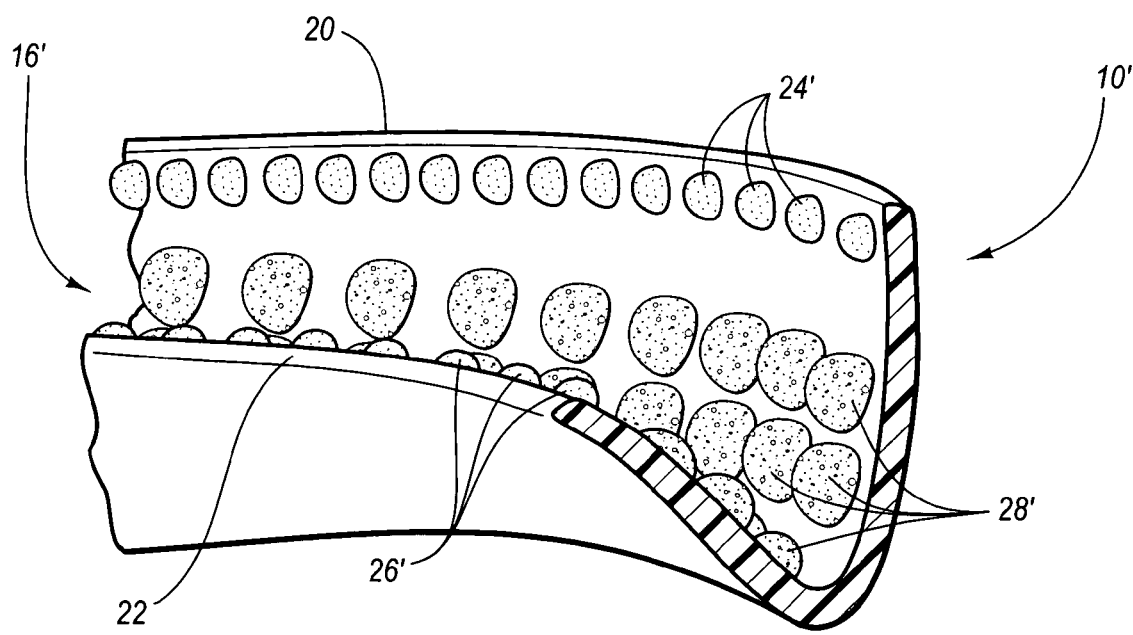
FIG. 2B is a cross-sectional view of en exemplary bleaching device according to the invention that includes a barrier layer, multiple spots or regions of a dental bleaching composition, and multiple spots or regions of a protective adhesive composition nearer the tray rim.

FIG. 2B alternatively depicts a dental bleaching device 10' that includes a barrier layer 18, regions or spots of a first protective adhesive composition 24', regions or spots of a second protective adhesive composition 26', and regions or spots of a dental bleaching composition 28' between the first and second adhesive compositions 24', 26'. Both the protective adhesive compositions 24', 26' and the dental bleaching composition 28' are located adjacent to the barrier layer. In this way, the protective adhesive compositions 24', 26' and dental bleaching composition 28' do not initially touch prior to use, thereby preventing or inhibiting contact between a bleaching agent activator that may optionally be included within one or more regions or spots of the protective adhesive compositions 24', 26' and the bleaching agent within the bleaching composition 28' prior to use.

Figure 3:
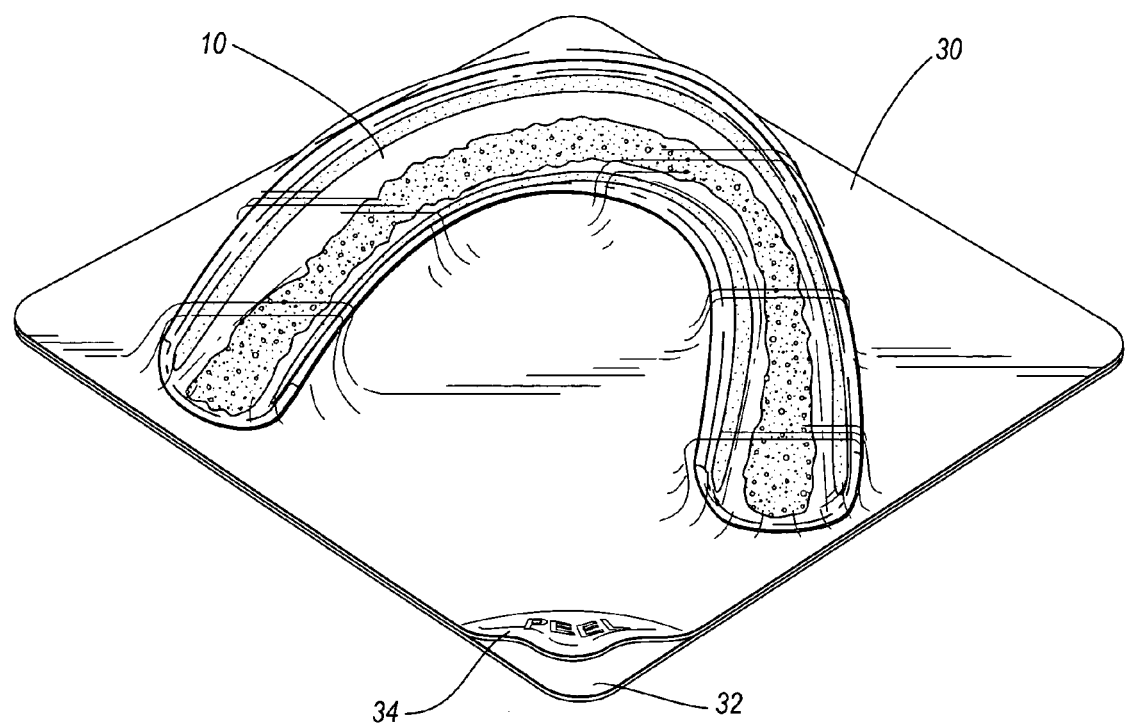
FIG. 3 illustrates a dental bleaching device according to the invention contained within a sealed protective package having a peelable cover.

In order to protect dental bleaching devices according to the invention from contaminants during storage and prior to use, the bleaching devices can be packaged within a sealed container or package. As illustrated in FIG. 3, a bleaching device 10 according to the invention can be sealed within a protective package 30 that includes a rigid support layer 32 and a peelable cover 34. When it is desired to use the bleaching device 10, the peelable cover 34 is removed and the bleaching device 10 is removed or separated from the support layer 32.

In one embodiment, the support layer 32 includes a shaped portion that acts as exoskeleton to hold or maintain the bleaching device 10 in the shape of a dental tray, or within a tray-like configuration, prior to use. In use, both the bleaching device 10 and support layer 32 are placed into a person's mouth so as to initially position the bleaching device over the person's teeth. Thereafter, the support layer 32 is removed, leaving only the bleaching device 10 within the person's mouth. This permits further manipulation of the barrier layer 18 in order for the bleaching device 10 to better conform to the shape and irregularities of the person's teeth.

In addition to, or instead of, the protective package 30, the bleaching device may alternatively include a removable protective layer (not shown) that is temporarily placed within the trough adjacent to the dental bleaching composition and protective adhesive composition. When it is desired to use the bleaching device, the removable protective layer is removed so as to expose the bleaching composition and protective adhesive composition.

Figure 4:
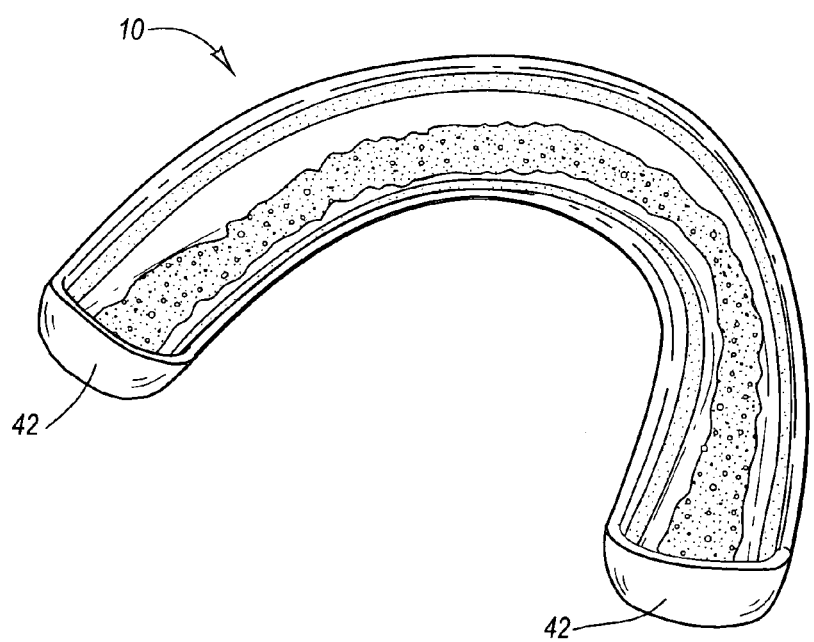
FIG. 4 is a perspective view of an exemplary dental bleaching device similar to the bleaching device depicted in FIG. 1, but that further includes a terminal side wall on each longitudinal end.

FIG. 4 illustrates a dental bleaching device 40 that is a variation of the U-shaped dental bleaching device 10 of FIGS. 1 and 2A. The main difference is that each longitudinal end 42 of the dental bleaching device 40 is raised so as to at least partially enclose the last tooth on each side of a person's dental arch when the bleaching device 40 is in use.

Figure 5:
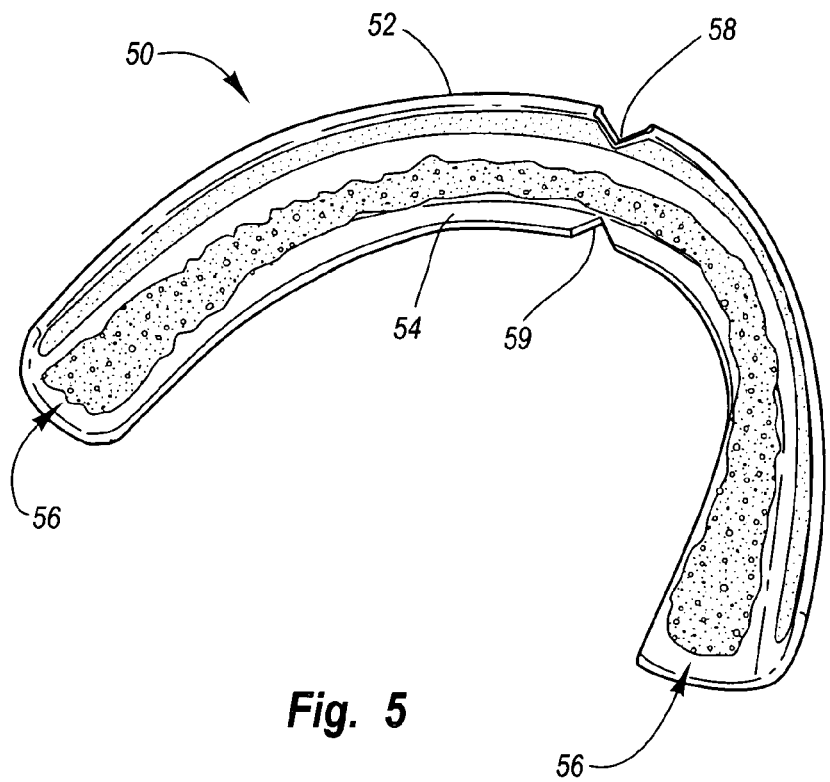
FIG. 5 is a perspective view of an exemplary dental bleaching device having an L-shaped trough, a curved longitudinal profile, and notches in the rims.

FIG. 5 illustrates an alternative embodiment of a dental bleaching device 50 according to the invention that has an L-shaped cross section. More particularly, the dental bleaching device 50 includes a front side wall 52 and a rear side wall 54 extending laterally from the front side wall 52 so as to form a trough 56 having an approximate L-shaped cross section. The L-shaped bleaching device 50 of FIG. 5 is somewhat easier to initially place over a person's dental arch compared to the U-shaped bleaching composition or devices of FIGS. 1–4. This is due to the approximately planar orientation of the rear side wall 54 relative to the occlusal or incisal edges of a person's teeth when the front side wall 52 of the dental bleaching device 50 is initially placed and adhered against the front surfaces of a person's teeth. On the other hand, more manipulation of the L-shaped bleaching device 50 is generally required to form and adhere to the rear side wall 54 against the lingual surfaces of the person's teeth as a result of the greater initial offset angle between the front side wall 52 and rear side wall 54. However, the ability of dental bleaching devices according to the invention to adhere to tooth surfaces immediately after placement over a person's teeth facilitates the process of conforming the front side wall 52 and rear side wall 54 to the person's tooth surfaces.

In the case of the dental bleaching device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped bleaching device is folded back against the lingual tooth surfaces during use, it can be readily seen that a bleaching device having an L-shaped trough is merely a variation of a bleaching device having a V-shaped trough. Thus, for purposes of this disclosure and the appended claims, the side wall 54 shall constitute, and fall within the definition of, a "rear side wall".

To facilitate the ability of a dental bleaching device to conform to the varying shapes and sizes among dental arches, the dental bleaching device may include mechanical features such as one or more notches within the front or rear side walls. As shown in FIG. 5, a dental bleaching device 50 includes a notch 58 near the center of the rim of the front side wall 52 and a notch 59 near the center of the rim of the rear side wall 54. Notches 58 and 59 allow the tray-like bleaching or device to more easily spread open or compress when being conformed to differently-sized dental arches. In this way, the dental bleaching device 50 can more easily be a "one-size fits all" composition or device.

Figure 6:
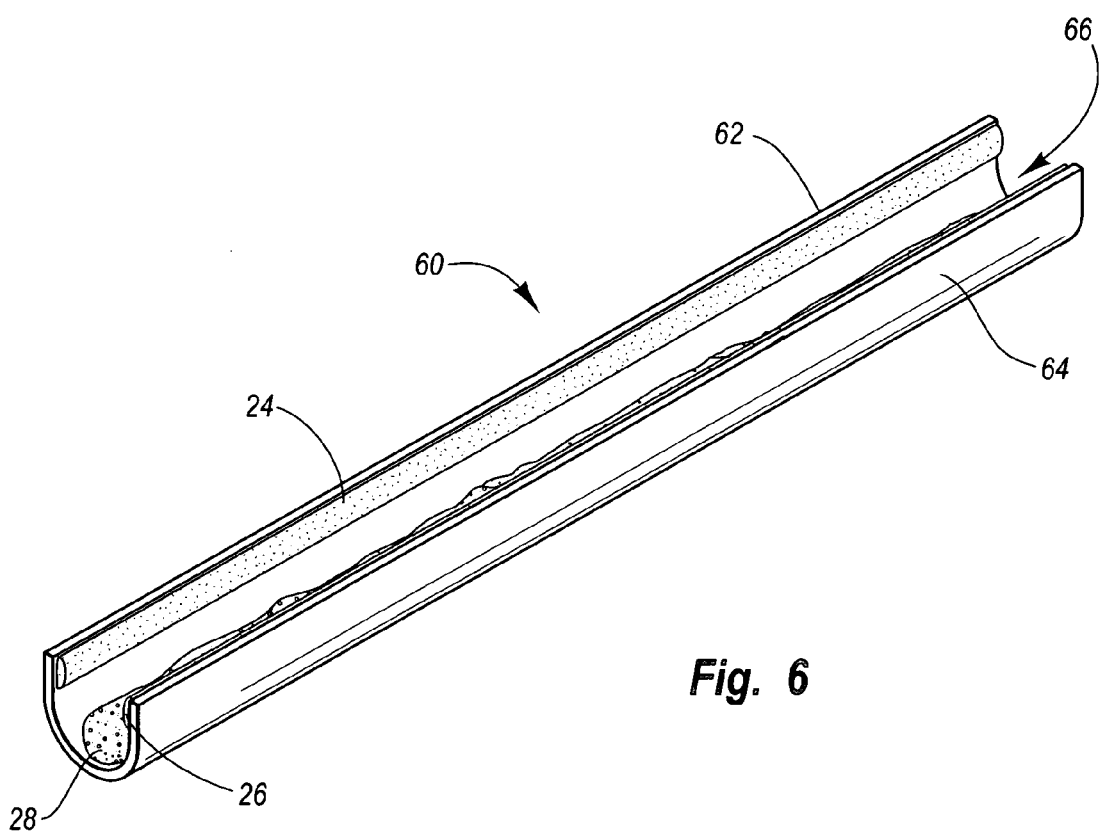
FIG. 6 is a perspective view of an exemplary dental bleaching device having a U-shaped trough and a substantially straight longitudinal profile.

FIG. 6 depicts an alternative embodiment of a dental bleaching device 60 according to the invention, which includes a front side wall 62 and a rear side wall 64 that define a U-shaped trough 66 into which a bead of bleaching gel 28 is placed. Instead of being horseshoe shaped like the dental bleaching device of FIGS. 1–5, or otherwise having a curved longitudinal profile, the dental bleaching device 60 of FIG. 6 has a substantially straight or linear longitudinal profile.

Figure 7:
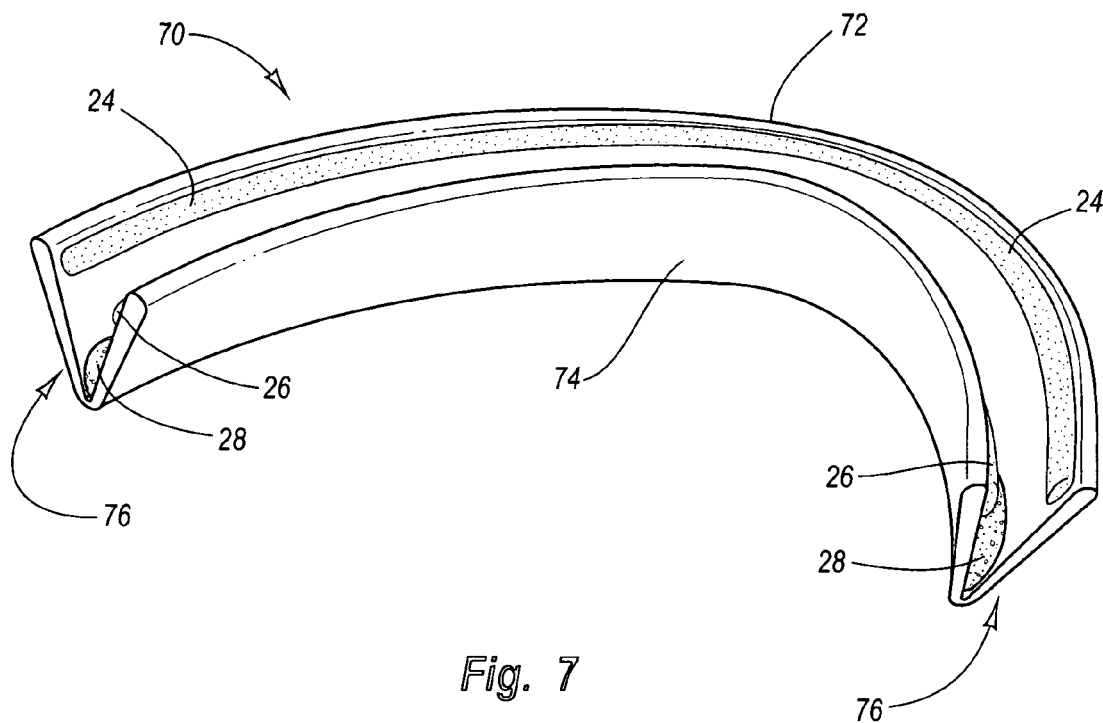
FIG. 7 is a perspective view of an exemplary dental bleaching device having a V-shaped trough and a curved longitudinal profile.

FIG. 7 depicts yet another alternative embodiment of a dental bleaching device 70 according to the invention. The dental bleaching device 70 includes a front side wall 72 and a rear side wall 74 that define a V-shaped trough 76 and a curved longitudinal profile. The main difference between the V-shaped bleaching device 70 of FIG. 7 and the L-shaped bleaching device 50 of FIG. 5 is the angle at which the front and rear side walls are laterally offset from each other.

Figure 8:
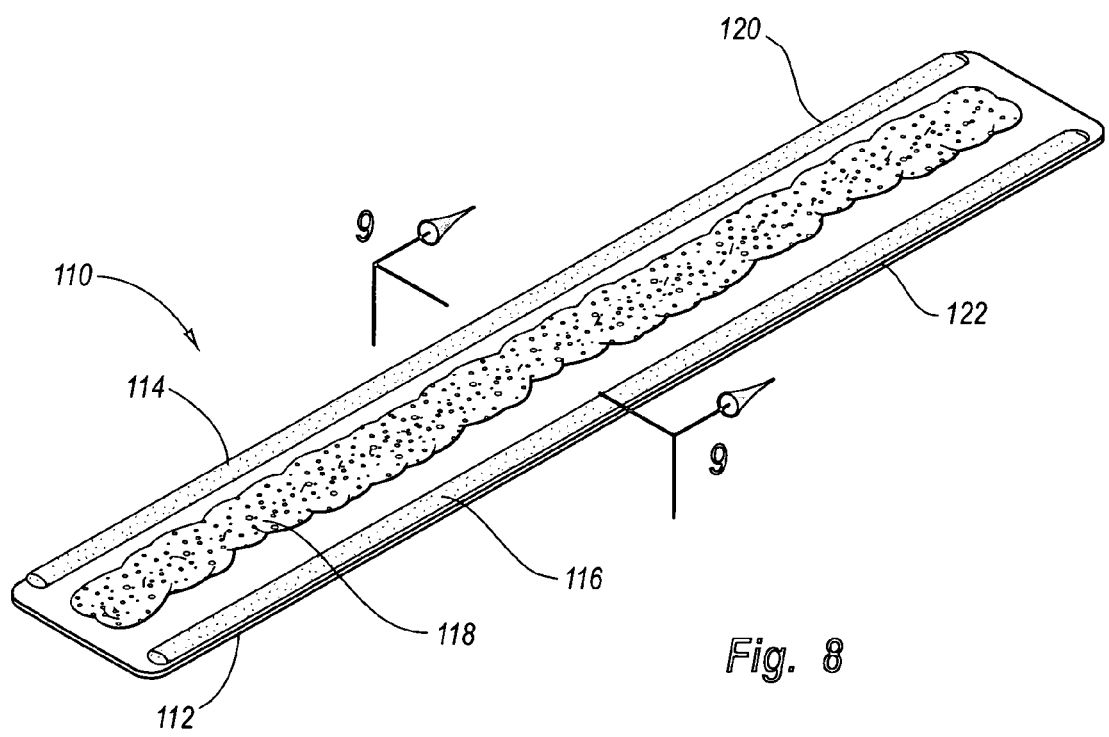
FIG. 8 is a perspective view of an exemplary dental bleaching device according to the invention in the shape of a strip or patch comprising a barrier layer, a dental bleaching composition, and a protective adhesive composition nearer the front and back edges.

Alternative embodiments of dental bleaching compositions and devices in the form of a strip or patch are depicted in FIGS. 8–11. FIG. 8 is a perspective view of a bleaching strip or patch 110 comprising a barrier layer 112, which preferably comprises a moisture-resistant material, a first protective adhesive composition or region 114, a second protective adhesive composition or region 116, and a dental bleaching composition 118. FIG. 9A is a cross-sectional view of the bleaching strip or patch 110 of FIG. 8 taken along cutting line 9A—9A.

It is within the scope of the invention for the bleaching gel 118 to directly contact the protective adhesive compositions 114, 116, the barrier layer 112, or both depending on where the bleaching composition 118 is located relative to the protective adhesive compositions or regions 114, 116. It is also within the scope for some or all of one or both of protective adhesive compositions or regions 114, 116 to be placed over a portion of the bleaching composition 118.

A first edge 120 of the bleaching strip 110 can be designed so as to terminate at or shy of the labial gingival margin of a person's dental arch when in use, and a second edge 122 can be designed so as to terminate at or shy of the lingual gingival margin of the person's dental arch when in use. Alternatively, the first and second edges 120, 122 can be designed so as to extend beyond one or both the labial and lingual gingival margins and overlap one or both of the labial and lingual gums. The second edge 122 may alternatively be spaced-apart from the first edge 120 in order to terminate well shy of the lingual gingival margin, or even at or near the occlusal edges of the user's teeth so as to obviate the need to include the second adhesive composition or region 116.

Figure 9A:
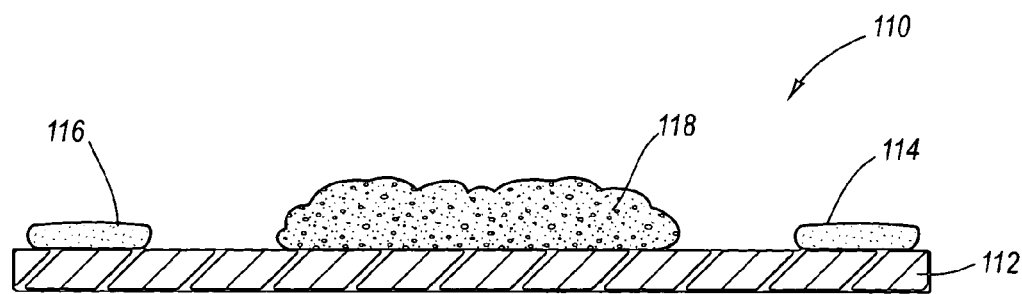
FIG. 9A is a cross-sectional view of the dental bleaching device of FIG. 8.
Figure 9B:
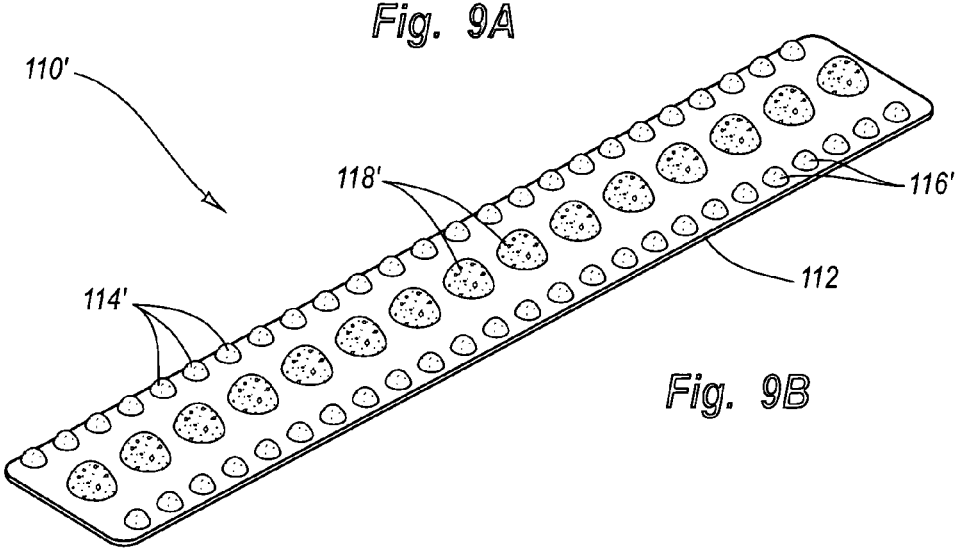
FIG. 9B is a perspective view of an exemplary bleaching device according to the invention that includes a barrier layer, multiple spots or regions of a dental bleaching composition, and multiple spots or regions of a protective adhesive composition nearer the front and back edges.

FIG. 9B alternatively depicts a dental bleaching device 110' that includes a barrier layer 112, regions or spots of a first protective adhesive composition 114', regions or spots of a second protective adhesive composition 116', and regions or spots of a dental bleaching composition 118' between the first and second protective adhesive compositions or regions 114', 116'. Both the protective adhesive compositions or regions 114', 116' and the dental bleaching composition 118' are located adjacent to the barrier layer 112. In this way, the protective adhesive compositions 114', 116' and dental bleaching composition 118' do not initially touch prior to use, thereby preventing or inhibiting contact between an optional bleaching agent activator within one or more spots or regions within one or both protective adhesive compositions 114', 116' and the bleaching agent within the bleaching composition 118' prior to use.

Figure 10:
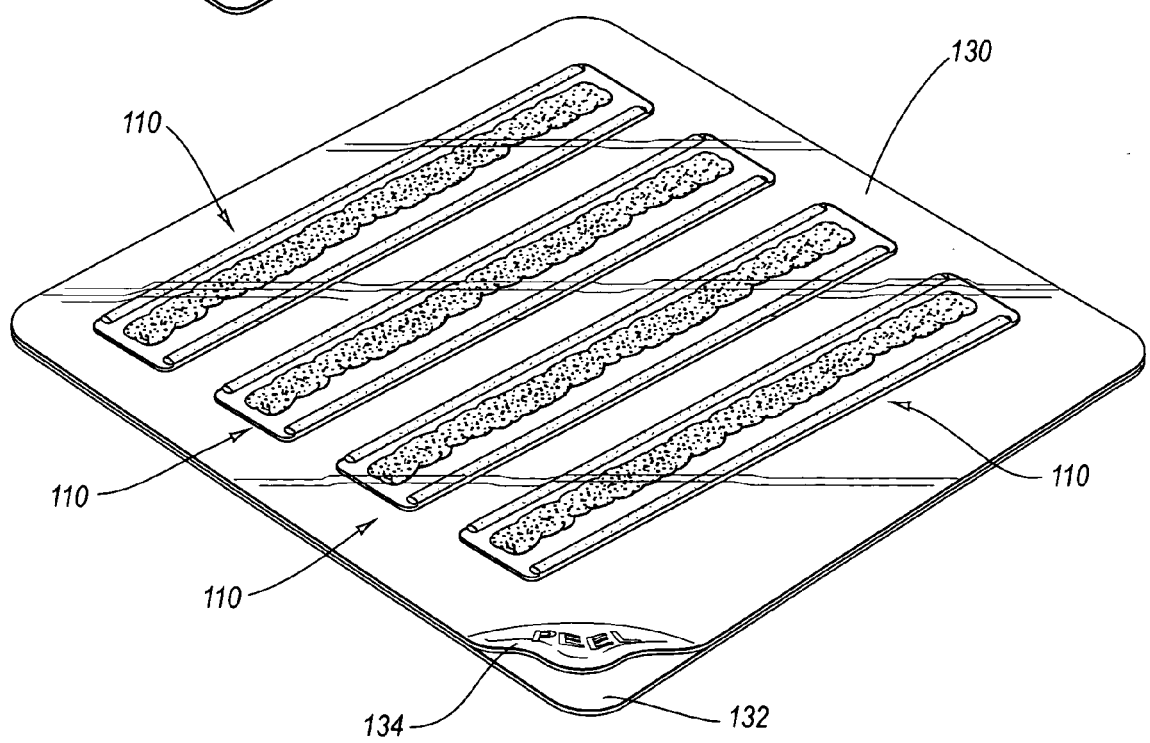
FIG. 10 illustrates multiple bleaching strips or patches according to the invention contained within a sealed, protective package having a peelable cover.

In order to protect bleaching strips or patches according to the invention from contaminants during storage and prior to use, they can be packaged within a sealed container or package. As illustrated in FIG. 10, one or more bleaching strips or patches 110 can be sealed within a protective package 130 that includes a rigid support layer 132 and a peelable cover 134. When it desired to use the bleaching strip or patch 110, the peelable cover 134 is removed and the bleaching strip 110 is removed or separated from the support layer 132. In addition to, or instead of, the protective package 130, the bleaching strip 110 may alternatively include a removable protective layer (not shown) that is temporarily placed adjacent to the bleaching composition and protective adhesive compositions. When it is desired to use the bleaching strip, the removable protective layer is removed so as to expose the bleaching and adhesive compositions.

Figure 11:
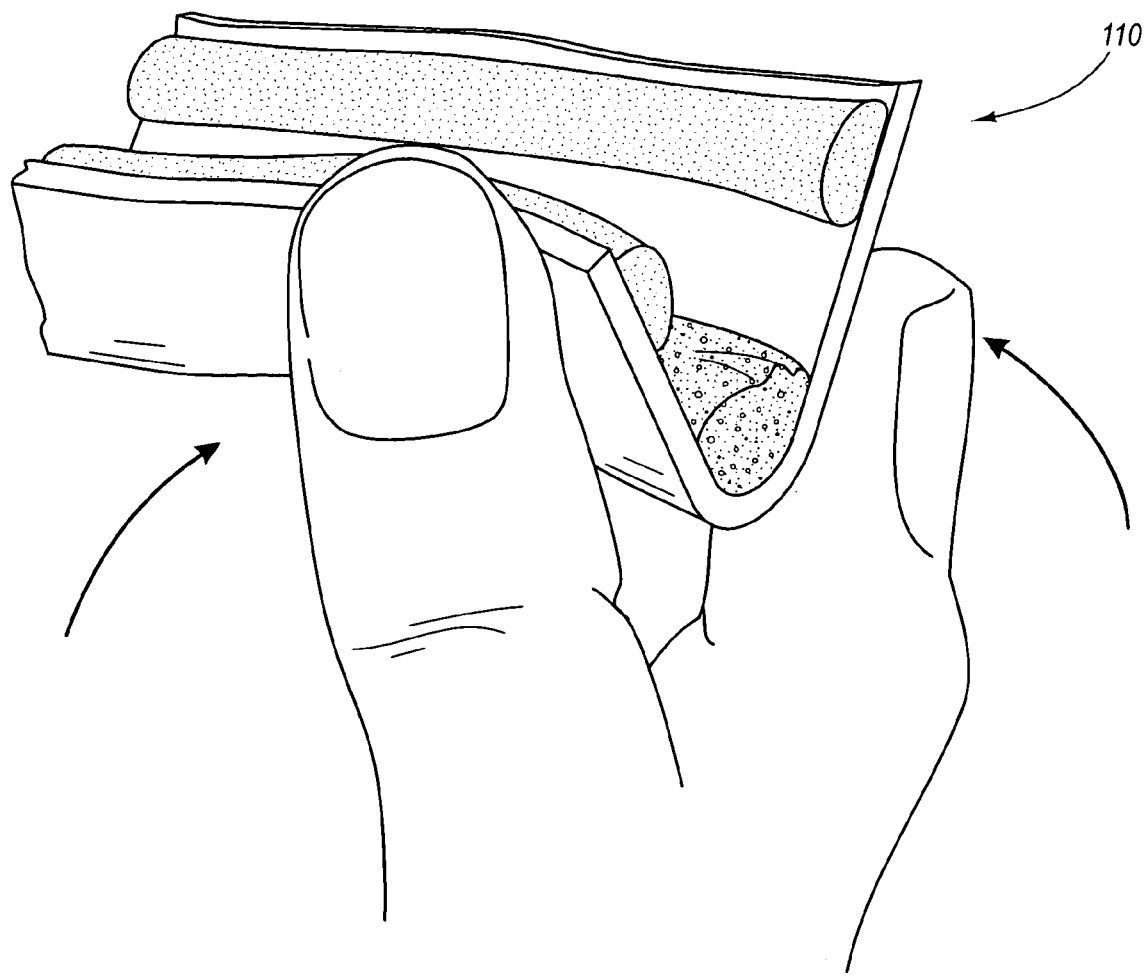
FIG. 11 illustrates a bleaching strip or patch according to the invention being manipulated so as to have an approximate V-shaped cross section prior to placement over a person's teeth.

FIG. 11 shows a bleaching strip or patch 142 being optionally manipulated (such as by bending, curving or folding) so as to have an approximate V-shaped cross section in order to facilitate placement of the bleaching strip or patch 142 over a person's teeth and/or gums.

Notwithstanding the foregoing examples, it will be appreciated that dental bleaching devices according to the invention can have any profile and longitudinal shape (e.g., they can be flat or have a 3-dimensional shape; they can have a straight or curved longitudinal profile from one end to the other). The front and rear side walls of a tray may define a trough of any desired cross-sectional shape (e.g., the trough can be trapezoidal, rectangular, or any other desired geometric shape).

The size and shape of dental bleaching devices according to the invention can be tailored to more readily fit either a person's upper dental arch or lower dental arch. They can be sized so as to bleach all or merely a subset of a person's teeth. The dental bleaching devices may be sufficiently adhesive and flexible so as to readily conform to a wide variety of differently-sized teeth and dental arches. The dental bleaching devices may be designed so as to substantially cover the front and lingual surfaces of the teeth to bleached. Bleaching the front and lingual surfaces helps to bleach the interproximal spaces between a person's teeth and yields more esthetically appealing teeth, although it is certainly within the scope of the invention to bleach more of one surface than another.

III. Methods of Making Dental Bleaching Compositions and Bleaching Devices Incorporation such Compositions The various components that make up the inventive dental bleaching devices according to the invention can be assembled or brought together in any desired order. In the case where both the dental bleaching composition and protective adhesive composition are a gel, one or both compositions can be placed directly adjacent to the barrier layer, whether in the shape of a dental tray, a strip or patch, or some other configuration, to yield the final dental bleaching device. The bleaching and adhesive compositions can be placed on the barrier layer simultaneously or sequentially. Some or all of the protective adhesive composition may be placed over a portion of the bleaching composition already placed against the barrier layer and/or some or all of the bleaching composition may be placed over a portion of the protective adhesive composition already placed against the barrier layer. The resulting bleaching device comprising the bleaching and protective adhesive compositions in gel form can be used as is, or they may be heated or otherwise processed so as to remove at least a portion of a solvent or carrier so as to yield bleaching and/or protective adhesive compositions that are substantially solid.

Alternatively, at least a portion of one or both of the bleaching and protective adhesive compositions can be placed against the barrier layer in gel form and then processed to remove at least a portion of the solvent or carrier. Thereafter, the remaining portion(s) of the bleaching and/or protective adhesive compositions are placed in gel form adjacent to the barrier and/or the previously placed composition(s). The resulting bleaching device can be used as is or further processed to remove additional solvent or carrier from the subsequently placed compositions(s).

In another embodiment, some of all of the dental bleaching composition and/or protective adhesive composition can be formed into a substantially solid sheet, a dental tray, or other desired shape without a barrier layer, e.g., by forming one or more gel compositions and then heating or otherwise processing the gel composition(s) to yield a substantially solid composition having a desired shape. Thereafter, a barrier layer is placed against the substantially solid composition to yield a bleaching device.

The barrier layer can have a desired shape prior to placing the bleaching and protective adhesive compositions as desired to yield the finished bleaching device. Alternatively, the barrier can be in the form of a sheet, the bleaching and protective adhesive compositions are placed as desired, and the resulting intermediate product cut, shaped or otherwise reconfigured into a desired shape of the dental bleaching device.

IV. Methods of Using Dental Bleaching Compositions and Bleaching Devices Incorporating such Compositions The dental bleaching devices according to the invention can be designed to be worn for any desired time period. Increasing the concentration of dental bleaching agent generally reduces the time required to effect bleaching. Nevertheless, due to the extremely comfortable fit and reliable adhesion between the inventive dental bleaching devices and the person's teeth, it is possible to wear such devices for extended periods of time in order to ensure more uniform bleaching. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

The dental bleaching devices according to the invention may be worn over a person's upper dental arch, lower dental arch, or both simultaneously. The ability to reliably and comfortably wear dental bleaching devices over the upper and lower dental arches simultaneously is another departure from bleaching strips, which are not recommended for use in bleaching the upper and lower dental arches at the same time.

Figure 12:
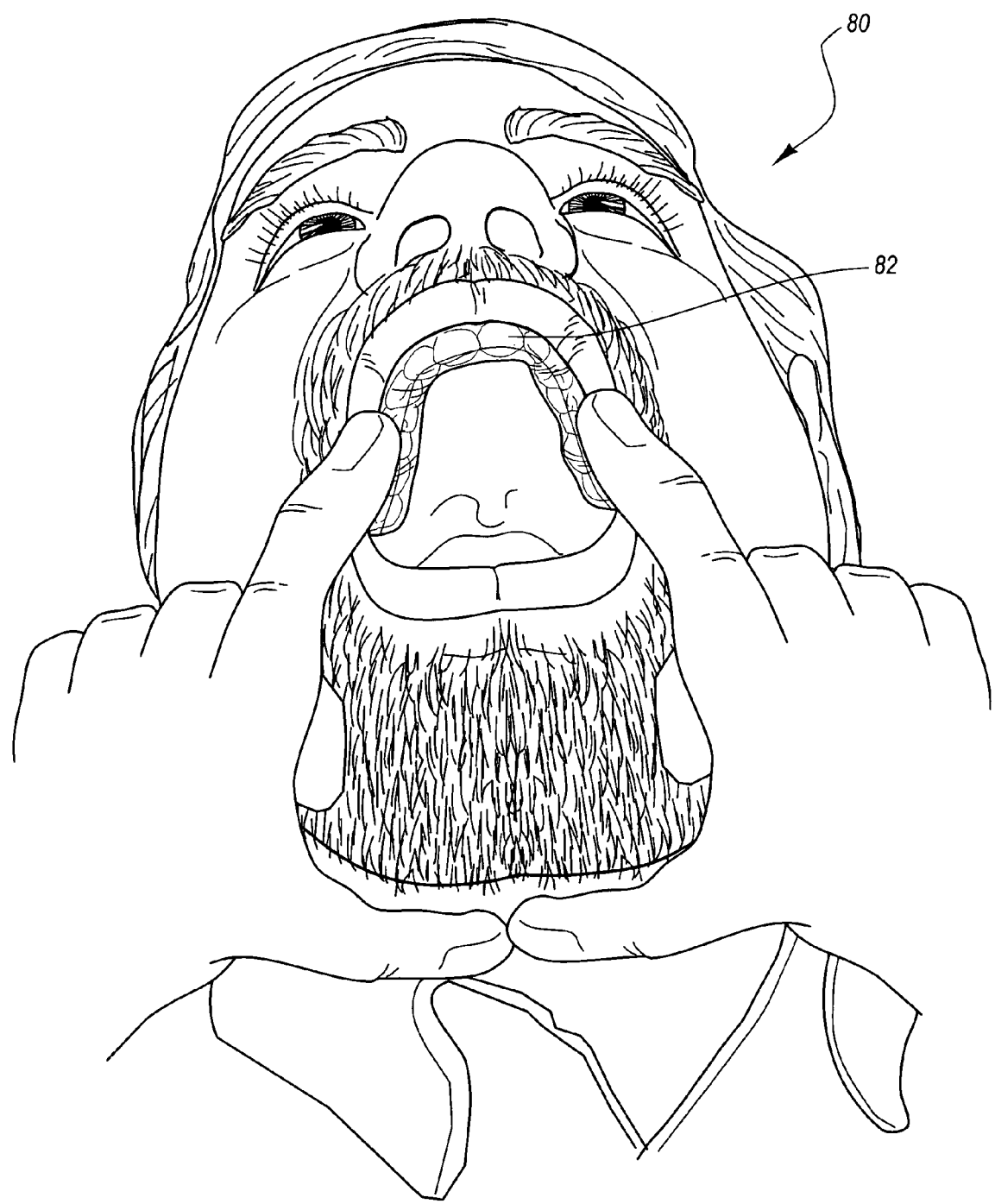
FIG. 12 illustrates a person placing a dental bleaching device according to one embodiment of the invention over the upper dental arch.
Figure 13:
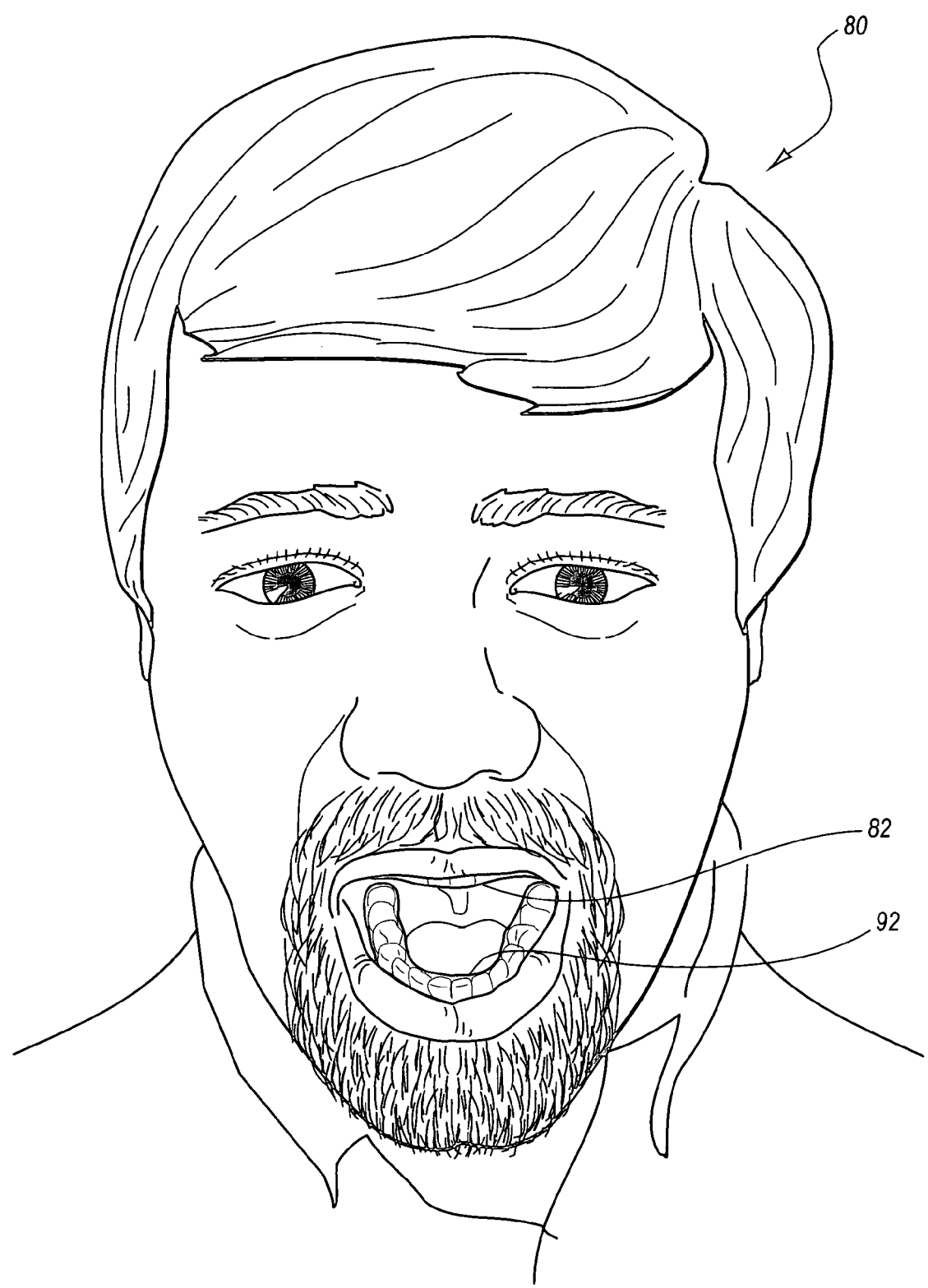
FIG. 13 illustrates a person after placing a dental bleaching device according to one embodiment of the invention over the lower dental arch, with a dental bleaching device already placed over the upper dental arch.

FIG. 12 illustrates a person 80 placing a dental bleaching device 82 over the person's upper dental arch. The dental bleaching device 82 can be in the form of a dental tray, strip, patch or other desired shape. FIG. 13 shows the person 80 with both a dental bleaching device 92 over the person's lower dental arch and the dental bleaching device 82 over the upper dental arch. It will be appreciated that the dental bleaching devices 82, 92 can be placed over a person's upper and lower dental arches in any desired order.

Figure 14A:
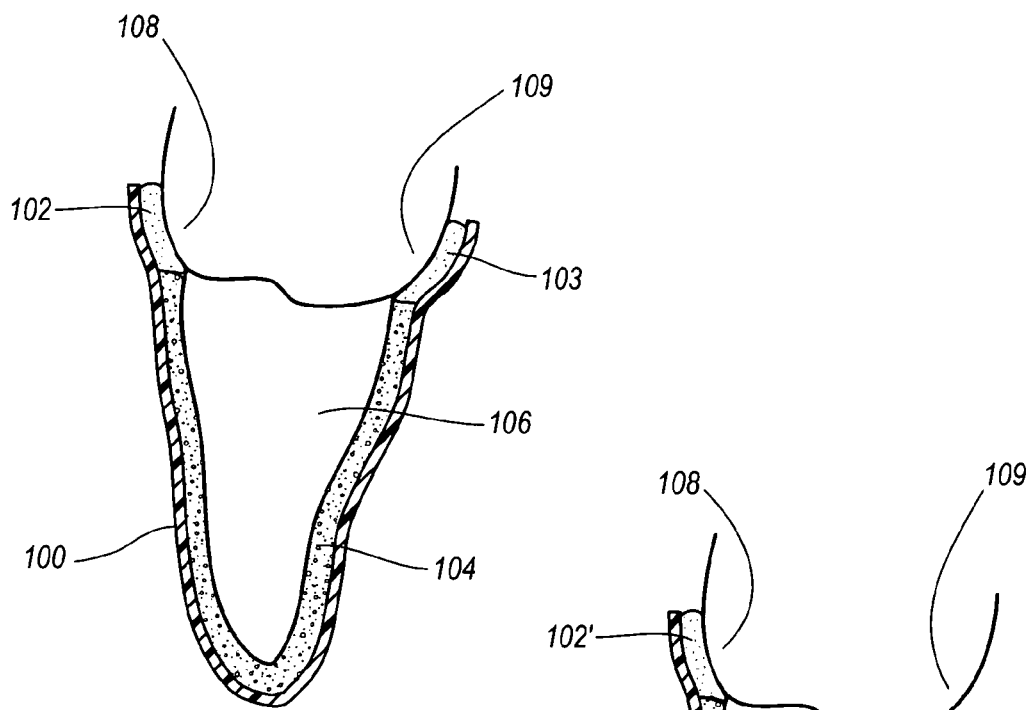
FIG. 14A is a cross-sectional view illustrating a dental bleaching device according to the invention covering the labial and lingual surfaces of a tooth, with a bleaching gel in contact with both surfaces and a protective adhesive composition in contact with and protecting both the labial and lingual gums at the gingival margin.
Figure 14B:
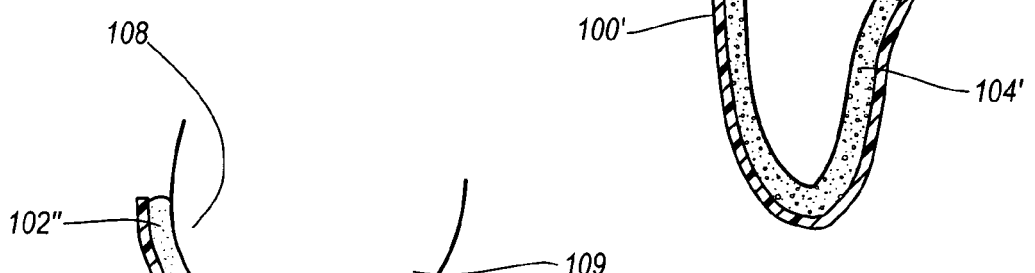
FIG. 14B is a cross-sectional view illustrating a dental bleaching device according to the invention covering the labial surface and part of the lingual surface of a tooth, with a bleaching gel in contact with both surfaces and a protective adhesive composition in contact with and protecting the labial gum at the gingival margin.
Figure 14C:
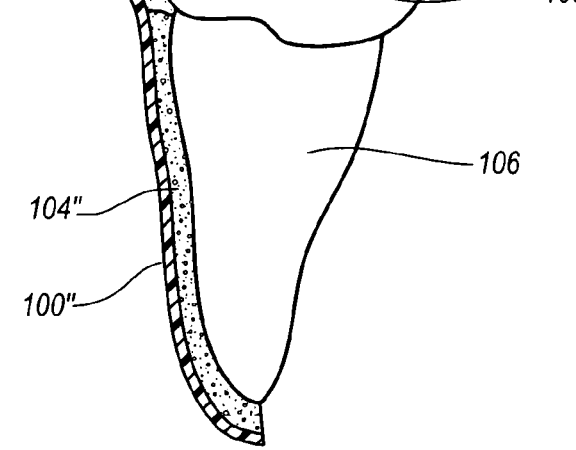
FIG. 14C is a cross-sectional view illustrating a dental bleaching device according to the invention that only covers the labial surface of a tooth, with a bleaching gel in contact with that surface and a protective adhesive composition in contact with and protecting the labial gum at the gingival margin.

As illustrated in FIGS. 14A–14C, the dental bleaching device may cover both surfaces of a person's teeth, all of one surface and part of another surface, or just one surface. FIG. 14A depicts a dental bleaching device 100 that is designed so as to cover both the labial and lingual surfaces of a tooth 106, as well as extend beyond the labial and lingual gingival margins 108, 109. A first protective adhesive composition or region 102 contacts and adheres to the labial gums at the labial gingival margin 108 and a second protective adhesive composition or region 103 contacts and adheres to the lingual gums at the lingual gingival margin 109 so as to protect them from the bleaching composition 104, which is confined to a region where it only contacts the labial and lingual surfaces of the patient's tooth 106.

FIG. 14B depicts another embodiment in which a dental bleaching device 100' is designed so as to cover all of the labial surfaces of teeth 106 and overlap the labial gingival margin 108 but only cover a portion of the lingual surfaces of teeth 106. A protective adhesive composition or region 102' contacts and adheres to the labial gums so as to protect them from the bleaching composition 104', which is confined to a region where it only contacts the labial tooth surfaces and a portion of the lingual tooth surfaces. Because the bleaching device 100' terminates well shy of the lingual gingival margin 109, no second protective adhesive composition or region is provided.

FIG. 14C depicts another embodiment in which a dental bleaching device 100" is designed so as to only cover the labial surfaces of teeth 106 and overlap the labial gingival margin 108. A protective adhesive composition or region 102" contacts and adheres to the labial gums so as to protect them from the bleaching composition 104", which is confined to a region where it only contacts the labial tooth surfaces.

In the case where the protective adhesive composition contains a bleaching agent activator, contacting the bleaching composition and/or protective adhesive composition with saliva or water causes the bleaching agent activator to leach or diffuse out of the protective adhesive composition, or otherwise become available, so as to react with or otherwise destabilize the bleaching agent within the dental bleaching composition in order to accelerate bleaching. In order to prevent or inhibit premature activation of the dental bleaching agent prior to use, the bleaching composition may advantageously be initially substantially anhydrous in order to prevent or inhibit diffusion or leaching of the bleaching agent activator from the protective adhesive composition into the bleaching composition. Alternatively, the bleaching composition may include a stabilizing agent, such as EDTA, in a quantity sufficient to prevent premature activation of the bleaching agent prior to use but not so much as to entirely prevent activation during use. In another embodiment, the bleaching composition may be positioned so as to not touch the protective adhesive composition prior to use, thereby preventing or inhibiting contact between the bleaching composition and protective adhesive composition prior to use.

To remove the dental bleaching device, a user can pry open a corner of the barrier layer using a fingernail or rigid tool and then pull the remainder off. Any residual bleaching and/or protective adhesive composition that remains adhered to the person's teeth can be removed by washing or flushing water over the person's teeth, and/or by brushing. Although the inventive bleaching and protective adhesive compositions can be very adhesive to teeth when protected from excessive moisture, they can be formulated to quickly break down and dissolve when flushed with excess water and/or by gentle mechanical action (e.g., brushing).

The dental bleaching devices can be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions according to the invention may be repeated as many times as needed to obtain a desired degree of tooth bleaching. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Bleaching Kits

For convenience of use, multiple dental bleaching devices may be packaged together and sold as a kit. In one embodiment, the number of dental bleaching devices provided with each kit may equal the number of sessions that represent a prescribed bleaching regimen. Because of the ease of placing the inventive dental bleaching devices over a person's teeth, coupled with the reliability with which they adhere to teeth, the likelihood that a particular bleaching device will fail, or otherwise not work as intended, is greatly diminished compared to conventional bleaching strips.

To efficiently utilize the space within a kit package, multiple dental bleaching devices can be stacked or interested together. The dental bleaching devices can be sealed collectively or individually as desired. A protective package 30 is depicted in FIG. 3, and a protective package 130 is depicted in FIG. 10. The bleaching devices may optionally contain a removable protective layer on an interior surface to protect the bleaching composition and protective adhesive composition from contamination or moisture.

It is within the scope of the invention to provide barrier layers, bleaching compositions, and protective adhesive compositions that are initially separate and that are brought together by the end user. For example, flowable bleaching and protective adhesive compositions can be expressed onto the barrier layer. The resulting bleaching device can be used as is or the bleaching and/or adhesive compositions can be allowed to dry.

VI. Examples of the Preferred Embodiments

The following are several examples of dental bleaching compositions and protective adhesive compositions that can used in the manufacture of bleaching compositions, as well as bleaching devices made therefrom. The exemplary formulations and manufacturing conditions are given by way of example, not by limitation, in order to illustrate dental bleaching devices that have been found to be useful for bleaching a person's teeth. Unless otherwise indicated, all percentages are by weight.

Examples 1–21 are directed to the manufacture of dental bleaching compositions that can be used as is or further processed to yield substantially solid bleaching compositions, both of which can be used to manufacture bleaching devices according to the invention. Examples 22–26 are directed to the manufacture of dental desensitizing compositions that can be used as is as protective adhesive compositions or further processed to yield substantially solid compositions, both of which can be used to manufacture bleaching devices according to the invention. Examples 27–29 are directed to the manufacture of medicament compositions that can be used as is as protective adhesive compositions or further processed to yield substantially solid compositions, both of which can be used to manufacture bleaching devices according to the invention. Examples 30–37 are directed to the manufacture of adhesive compositions that do not include any active agent. Examples 38–43 are directed to exemplary dental bleaching gels that are suitable for use in manufacturing dental bleaching devices according to the invention. Examples 44–49 describe further variations of exemplary dental bleaching compositions according to the invention.

EXAMPLE 1

A dental bleaching composition was formed by mixing together the following components:

| | |
|---|---|
| Carbamide Peroxide | 16% |
| Polyvinyl pyrrolidone (M.W. = 1.3 million) | 38% |
| Water | 46% |

The dental bleaching composition was spread in the form of a gel over flexible polymer sheets using a spatula and then heated in a forced air oven heated to a temperature of 50–70° C. for approximately 1 hour. The coated sheets were removed from the oven and inspected. The bleaching gel had dried sufficiently so as to form a substantially solid, coherent bleaching composition on the surface of the polymer sheets. The coated sheets were placed back into the oven overnight to remove additional water.

The coated sheets were removed from the oven a second time, cut apart into smaller-sized pieces, and either used as strips or shaped into tray-like devices suitable for placement over a person's teeth.

A protective adhesive composition is placed over a portion of the substantially solid bleaching composition near one or both rims of a tray-like device, or near one or both edges of a strip, to yield a bleaching device according to the invention. The device is used as is or further heated to yield a substantially solid protective adhesive composition.

Alternatively, a protective adhesive composition is placed over a portion of the dental bleaching composition described initially (i.e., before heating in the forced air oven) to form a dental bleaching device that is used as is or further heated to cause at least a portion of the adhesive composition and bleaching composition to become substantially solid.

EXAMPLE 2

A dental bleaching composition was formed by mixing together the following components:

| | |
|---|---|
| Carbamide Peroxide | 16% |
| PolyOx WSR 101(M.W. = 1 million) | 7% |
| Water | 77% |

The bleaching composition and a protective adhesive composition are used to manufacture dental bleaching devices according to the procedures described in Example 1.

EXAMPLE 3

A dental bleaching composition was formed by mixing together the following components:

| | |
|---|---|
| Carbamide Peroxide | 16% |
| Carbopol 974P | 5% |
| Aqueous NaOH (50%) | 6% |
| Water | 73% |

The bleaching composition and a protective adhesive composition are used to manufacture dental bleaching devices according to the procedures described in Example 1.

EXAMPLE 4

A dental bleaching composition was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The bleaching composition and a protective adhesive composition are used to manufacture dental bleaching devices according to the procedures described in Example 1.

EXAMPLE 5

A dental bleaching composition was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The bleaching composition and a protective adhesive composition are used to manufacture dental bleaching devices according to the procedures described in Example 1.

EXAMPLE 6

A dental bleaching composition was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

The bleaching composition and a protective adhesive composition are used to manufacture dental bleaching devices according to the procedures described in Example 1.

EXAMPLE 7

A dental bleaching composition was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The bleaching composition and a protective adhesive composition are used to manufacture dental bleaching devices according to the procedures described in Example 1.

EXAMPLE 8

A dental bleaching composition was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The bleaching composition and a protective adhesive composition are used to manufacture dental bleaching devices according to the procedures described in Example 1.

EXAMPLE 9

A dental bleaching composition was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The bleaching composition and a protective adhesive composition are used to manufacture dental bleaching devices according to the procedures described in Example 1.

EXAMPLE 10

A dental bleaching composition was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The bleaching composition and a protective adhesive composition are used to manufacture dental bleaching devices according to the procedures described in Example 1.

EXAMPLE 11

A dental bleaching composition was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The bleaching composition and a protective adhesive composition are used to manufacture dental bleaching devices according to the procedures described in Example 1.

EXAMPLE 12

A dental bleaching composition was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The bleaching composition and a protective adhesive composition are used to manufacture dental bleaching devices according to the procedures described in Example 1.

EXAMPLE 13

A dental bleaching composition was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The bleaching composition and a protective adhesive composition are used to manufacture dental bleaching devices according to the procedures described in Example 1.

EXAMPLE 14

A dental bleaching composition was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The bleaching composition and a protective adhesive composition are used to manufacture dental bleaching devices according to the procedures described in Example 1.

EXAMPLE 15

A dental bleaching composition was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The bleaching composition and a protective adhesive composition are used to manufacture dental bleaching devices according to the procedures described in Example 1.

EXAMPLE 16

A dental bleaching composition was formed by mixing together the following components:

| | |
|---|---|
| Carbamide Peroxide | 15% |
| Polyvinyl pyrrolidone (M.W. = 1.3 million) | 32% |
| Water | 12.8% |
| Ethanol | 20% |
| Glycerin | 10% |
| Aerosil 200 | 5% |
| Calcium EDTA | 0.2% |
| Sodium Lauryl Sulfate | 5% |

The bleaching composition and a protective adhesive composition are used to manufacture dental bleaching devices according to the procedures described in Example 1.

EXAMPLE 17

A dental bleaching composition was formed by mixing together the following components:

| | |
|---|---|
| Carbamide Peroxide | 15% |
| Polyvinyl pyrrolidone (M.W. = 1.3 million) | 26% |
| Water | 16.8% |
| Ethanol | 25% |
| Glycerin | 15% |
| Calcium EDTA | 0.2% |
| Sodium Lauryl Ether Sulfate | 2% |

The bleaching composition and a protective adhesive composition are used to manufacture dental bleaching devices according to the procedures described in Example 1.

EXAMPLE 18

A dental bleaching composition was formed by mixing together the following components:

| | |
|---|---|
| Carbamide Peroxide | 15% |
| Polyvinyl pyrrolidone (M.W. = 1.3 million) | 32% |
| Water | 13.8% |
| Ethanol | 20% |
| Glycerin | 12% |
| Aerosil 200 | 5% |
| Calcium EDTA | 0.2% |
| Silwet L-7001 | 2% |

The bleaching composition and a protective adhesive composition are used to manufacture dental bleaching devices according to the procedures described in Example 1.

EXAMPLE 19

A dental bleaching composition was formed by mixing together the following components:

| | |
|---|---|
| Calcium Peroxide | 20% |
| Carbamide Peroxide | 4% |
| Polyvinyl pyrrolidone (M.W. = 1.3 million) | 20% |
| Water | 11.8% |
| Ethanol | 20% |
| Glycerin | 18% |
| Aerosil 200 | 5% |
| Calcium EDTA | 0.2% |
| Sodium Lauryl Sulfate | 2% |

The bleaching composition and a protective adhesive composition are used to manufacture dental bleaching devices according to the procedures described in Example 1.

EXAMPLE 20

A dental bleaching composition was formed by mixing together the following components:

| | |
|---|---|
| Carbamide Peroxide | 10% |
| Kollidon 90 (M.W. = 1.3 million) | 18.7% |
| Water | 42.3% |
| Ethanol | 13.3% |
| Glycerin | 12% |
| Aerosil 200 | 3.3% |
| Sodium Lauryl Sulfate | 0.33% |

The bleaching composition and a protective adhesive composition are used to manufacture dental bleaching devices according to the procedures described in Example 1.

EXAMPLE 21

A dental bleaching composition was formed by mixing together the following components:

| | |
|---|---|
| Carbamide Peroxide | 7.1% |
| Kollidon 90 (M.W. = 1.3 million) | 25% |
| Water | 10.7% |
| Ethanol | 50.7% |
| Glycerin | 2.9% |
| Aerosil 200 | 3.6% |

The bleaching composition and a protective adhesive composition are used to manufacture dental bleaching devices according to the procedures described in Example 1.

EXAMPLE 22

A dental desensitizing composition suitable for use in making a protective adhesive composition was formed by mixing together the following components:

| | |
|---|---|
| Sodium Fluoride | 0.25% |
| Polyvinyl pyrrolidone (M.W. = 1.3 million) | 30% |
| Water | 69.75% |

The desensitizing composition was spread in the form of a gel over flexible polymer sheets using a spatula and then heated in a forced air oven heated to a temperature of 50–70° C. for approximately 1 hour. The coated sheets were removed from the oven and inspected. The desensitizing gel had dried sufficiently so as to form a substantially solid, coherent desensitizing composition on the surface of the polymer sheets. The coated sheets were cut apart into smaller-sized pieces and either used as strips or shaped into tray-like devices suitable for placement over a person's teeth.

A bead of bleaching composition is placed over a portion of the substantially solid desensitizing composition so that a portion of the desensitizing composition extends beyond the bleaching composition near one or both rims of a tray-like device or near one or both edges of a strip to yield a bleaching device according to the invention. The desensitizing composition that extends beyond the bleaching composition forms a protective adhesive region. The bleaching device is used as is or further heated to yield a substantially solid bleaching composition.

Alternatively, a bleaching composition is placed over a portion of the desensitizing composition described initially (i.e., before heating in the forced air oven) to form a dental bleaching device that is used as is or further heated to cause at least a portion of the bleaching composition and desensitizing composition to become substantially solid. The desensitizing composition that extends beyond the bleaching composition, whether in gel or substantially solid form, forms a protective adhesive region.

EXAMPLE 23

A dental desensitizing composition suitable for use in making a protective adhesive composition was formed by mixing together the following components:

| | |
|---|---|
| Sodium Citrate | 5% |
| Polyvinyl pyrrolidone (M.W. = 1.3 million) | 20% |
| Water | 75% |

The desensitizing composition and a dental bleaching composition are used to manufacture dental bleaching devices according to the procedures described in Example 22.

EXAMPLE 24

A dental desensitizing composition suitable for use in making a protective adhesive composition was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The desensitizing composition and a dental bleaching composition are used to manufacture dental bleaching devices according to the procedures described in Example 22.

EXAMPLE 25

A dental desensitizing composition suitable for use in making a protective adhesive composition was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The desensitizing composition and a dental bleaching composition are used to manufacture dental bleaching devices according to the procedures described in Example 22.

EXAMPLE 26

A dental desensitizing composition suitable for use in making a protective adhesive composition was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The desensitizing composition and a dental bleaching composition are used to manufacture dental bleaching devices according to the procedures described in Example 22.

EXAMPLE 27

A medicament composition suitable for use in making a protective adhesive composition was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The medicament composition and a dental bleaching composition are used to manufacture dental bleaching devices according to the procedures described in Example 22.

EXAMPLE 28

A medicament composition suitable for use in making a protective adhesive composition was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The medicament composition and a dental bleaching composition are used to manufacture dental bleaching devices according to the procedures described in Example 22.

EXAMPLE 29

A medicament composition suitable for use in making a protective adhesive composition was formed by mixing together the following components:

| | |
|---|---|
| Phenol | 3% |
| Polyvinyl pyrrolidone (M.W. = 1.3 million) | 35% |
| Ethanol | 62% |

The medicament composition and a dental bleaching composition are used to manufacture dental bleaching devices according to the procedures described in Example 22.

EXAMPLE 30

An adhesive composition suitable for use in making a protective adhesive composition was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The adhesive composition and a dental bleaching composition are used to manufacture dental bleaching devices according to the procedures described in Example 22.

EXAMPLE 31

An adhesive composition suitable for use in making a protective adhesive composition was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The adhesive composition and a dental bleaching composition are used to manufacture dental bleaching devices according to the procedures described in Example 22.

EXAMPLE 32

An adhesive composition suitable for use in making a protective adhesive composition was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The adhesive composition and a dental bleaching composition are used to manufacture dental bleaching devices according to the procedures described in Example 22.

EXAMPLE 33

An adhesive composition suitable for use in making a protective adhesive composition was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The medicament composition and a dental bleaching composition are used to manufacture dental bleaching devices according to the procedures described in Example 22.

EXAMPLE 34

An adhesive composition suitable for use in making a protective adhesive composition was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The adhesive composition and a dental bleaching composition are used to manufacture dental bleaching devices according to the procedures described in Example 22.

EXAMPLE 35

An adhesive composition suitable for use in making a protective adhesive composition was formed by mixing together the following components:

| | |
|---|---|
| Ethanol | 63.6% |
| Glycerin | 9.1% |
| Polyvinyl pyrrolidone (M.W. = 1.3 million) | 27.3% |

The adhesive composition and a dental bleaching composition are used to manufacture dental bleaching devices according to the procedures described in Example 22.

EXAMPLE 36

An adhesive composition suitable for use in making a protective adhesive composition was formed by mixing together the following components:

| | |
|---|---|
| Ethanol | 44% |
| Polyvinyl pyrrolidone (M.W. = 1.3 million) | 34% |
| Glycerin | 14% |
| Sodium Lauryl Sulfate | 3% |
| Sucralose | 1% |
| Artificial Peach Flavor | 4% |

The adhesive composition and a dental bleaching composition are used to manufacture dental bleaching devices according to the procedures described in Example 22.

EXAMPLE 37

An desensitizing and remineralizing composition suitable for use in making a protective adhesive composition was formed by mixing together the following components:

| | |
|---|---|
| Ethanol | 31.95% |
| Water | 10% |
| Polyvinyl pyrrolidone (M.W. > 1 million) | 27% |
| Polyvinyl pyrrolidone (M.W. ≈ 60,000) | 10% |
| Sodium Lauryl Sulfate | 0.5% |
| Glycerin | 15% |
| Sucralose (25% solution) | 0.5% |
| Peach Flavor | 4% |
| Potassium Nitrate | 0.8% |
| Sodium Fluoride | 0.25% |

The desensitizing and remineralizing composition and a dental bleaching composition are used to manufacture dental bleaching devices according to the procedures described in Example 22.

EXAMPLE 38

A dental bleaching gel suitable for use in manufacturing dental bleaching devices according to the invention was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 (SiO$_2$) | 7% |
| Peach Flavor | 2% |
| Polyethylene Glycol (M.W. = 20,000) | 20% |

The dental bleaching gel was placed within a flexible, thin-walled dental tray. A protective adhesive composition is placed near at least one of the front and rear rims of the tray to yield a dental bleaching device according to the invention. The bleaching device is used as is or processed so at to remove a portion of the solvent within the bleaching gel and protective adhesive composition.

Alternatively, the dental bleaching gel and a protective adhesive composition are placed onto a barrier layer in the form of a strip or patch to yield a dental bleaching device according to the invention.

The bleaching gel and a protective adhesive composition are alternatively formed into dental bleaching devices according to one or more processes described in Examples 1 and 22.

EXAMPLE 39

A dental bleaching gel suitable for use in manufacturing dental bleaching devices according to the invention was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The bleaching gel and a protective adhesive composition are used to manufacture dental bleaching devices according to one or more procedures described in Examples 1, 22 and 38.

EXAMPLE 40

A dental bleaching gel suitable for use in manufacturing dental bleaching devices according to the invention was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The bleaching gel and a protective adhesive composition are used to manufacture dental bleaching devices according to one or more procedures described in Examples 1, 22 and 38.

EXAMPLE 41

A dental bleaching gel suitable for use in manufacturing dental bleaching devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The bleaching gel and a protective adhesive composition are used to manufacture dental bleaching devices according to one or more procedures described in Examples 1, 22 and 38.

EXAMPLE 42

A dental bleaching gel suitable for use in manufacturing dental bleaching devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The bleaching gel and a protective adhesive composition are used to manufacture dental bleaching devices according to one or more procedures described in Examples 1, 22 and 38.

EXAMPLE 43

A dental bleaching gel suitable for use in manufacturing dental bleaching devices according to the invention was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

The bleaching gel and a protective adhesive composition are used to manufacture dental bleaching devices according to one or more procedures described in Examples 1, 22 and 38.

EXAMPLE 44

Any of the dental bleaching compositions of Examples 1–21 and 38–43 are used together with any of the protective adhesive compositions of Examples 22–37 to form dental bleaching devices according to the invention.

EXAMPLE 45

Any of the protective adhesive compositions of Examples 22–37 used to manufacture bleaching devices according to Example 44 are modified by adding a bleaching agent in an amount that is less than the amount of bleaching agent within the bleaching composition manufactured according to one or more of Examples 1–21 and 38–43.

EXAMPLE 46

Any of the dental bleaching compositions of Examples 1–21 and 38–43 used to manufacture bleaching devices according to Examples 1–21 and 38–44 are modified by adding one or more of a desensitizing agent, remineralizing agent, antimicrobial agent, antiplaque agent, anti-tartar gent, or other medicament.

EXAMPLE 47

Any of the protective adhesive compositions of Examples 22–37 used to manufacture bleaching devices according to Examples 22–37 and 44 are modified by adding one or more of a colorant, gingival soothing agent, isotonic solution-forming salt, anesthetic, antioxidant, flavoring agent, preservative, mouth freshening agent, detergent, inorganic thickening agent, remineralizing agent, antiplaque agent, anti-tartar agent, freshening agent, or antioxidant.

EXAMPLE 48

Any of the dental bleaching devices manufactured according to Examples 1–46 are modified by providing a barrier layer in the form of a tray, strip or patch comprising a blend of ethyl vinyl acetate (80%) and polypropylene (20%).

EXAMPLE 49

Any of the protective adhesive compositions according to Examples 22–37 are modified by adding an effective amount of one or more bleaching agent activators (e.g., 5% of a an alkali metal or alkaline earth metal base and/or 1% of a metal, metal compound or organo-metallic enzyme).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental bleaching device, comprising:
   a barrier layer;
   a dental bleaching composition, positioned relative to said barrier layer so as to contact a person's teeth during use, comprising at least one dental bleaching agent; and
   a protective adhesive composition, positioned relative to said barrier layer and so as to shield a user's gums from said bleaching composition during use, comprising at least one tissue adhesion agent that includes at least one hydrophilic polymer, and said dental bleaching agent in a lower concentration than the dental bleaching agent contained in said dental bleaching composition.

2. A dental bleaching device as defined in claim 1, said barrier layer being flexible so as to readily conform to the shape of a person's teeth during use.

3. A dental bleaching device as defined in claim 1, said barrier layer comprising at least one of wax, metal foil, paraffin, ethylene-vinyl acetate copolymer, ethylene-vinyl alcohol copolymer, polycaprolactone, polyolefin, polyethylene, high density polyethylene, low density polyethylene, ultra-low density polyethylene, polypropylene, polytetrafluoroethylene, polyester, polycarbonate, polyurethane, polyamide, or polyesteramide.

4. A dental bleaching device as defined in claim 1, said barrier layer having a cross-sectional thickness in a range of about 0.025 mm to about 1.5 mm.

5. A dental bleaching device as defined in claim 1, said barrier layer having a cross-sectional thickness in a range of about 0.05 mm to about 1 mm.

6. A dental bleaching device as defined in claim 1, said barrier layer having a tray configuration comprising a least two sidewalls that define a trough within which the dental bleaching composition and protective adhesive composition reside prior to use.

7. A dental bleaching device as defined in claim 6, said barrier layer having a horse-shoe configuration prior to use so as to approximate the curvature of a person's dental arch.

8. A dental bleaching device as defined in claim 6, at least a portion of said trough having a cross section that is approximately U-shaped, V-shaped, L-shaped, rectangular, or trapezoidal.

9. A dental bleaching device as defined in claim 6, said barrier layer being sufficiently thin and flexible so as to be unable to maintain said tray configuration absent external support, the dental bleaching device further comprising a removable exoskeleton that maintains said barrier layer in said tray-like configuration prior to use.

10. A dental bleaching device as defined in claim 1, said barrier layer comprising a strip or patch prior to use.

11. A dental bleaching device as defined in claim 1, said barrier layer designed so as to approximately terminate at or near a person's gingival margin during use.

12. A dental bleaching device as defined in claim 1, said barrier layer designed so as to overlap a person's gingival margin during use.

13. A dental bleaching device as defined in claim 1, said dental bleaching composition further comprising a liquid or gel carrier so as to yield a sticky and viscous bleaching composition.

14. A dental bleaching device as defined in claim 1, said dental bleaching composition being substantially solid prior to use and becoming more adhesive to teeth or gums when moistened with saliva or water.

15. A dental bleaching device as defined in claim 1, said dental bleaching composition comprising a tissue adhesion agent that is at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

16. A dental bleaching device as defined in claim 1, said dental bleaching composition further comprising at least one member selected from the group comprising dental desensitizing agents, stabilizing agents, remineralizing agent, antimicrobial agents, antiplaque agents, and anti-tartar agents.

17. A dental bleaching device as defined in claim 1, said protective adhesive composition comprising a liquid or gel carrier so as to yield a sticky and viscous protective adhesive composition.

18. A dental bleaching device as defined in claim 1, said protective adhesive composition being substantially solid prior to use and becoming more adhesive to teeth when moistened with saliva or water.

19. A dental bleaching device as defined in claim 1, said hydrophilic polymer within said protective adhesive composition comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

20. A dental bleaching device as defined in claim 1, said protective adhesive composition further comprising at least one member selected from the group comprising dental desensitizing agents, remineralizing agent, antimicrobial agents, preservatives, antiplaque agents, anti-tartar agents, gingival soothing agents, anesthetics, antioxidants, flavorants, mouth freshening agents, detergents, and colorants.

21. A dental bleaching device as defined in claim 20, said protective adhesive composition comprising less than 10% by weight of said dental bleaching agent, and said bleaching composition comprising at least 10% by weight of said dental bleaching agent.

22. A dental bleaching device as defined in claim 1, further comprising a sealed package within which the dental bleaching device is sealed prior to use.

23. A dental bleaching device as defined in claim 1, further comprising a removable exoskeleton that maintains said barrier layer in a desired shape prior to use.

24. A dental bleaching device as defined in claim 1, said removable exoskeleton maintaining said barrier layer in the desired shape of a dental tray prior to use.

25. A kit for use in bleaching a person's teeth comprising a plurality of said dental bleaching devices according to claim 1.

26. A method for bleaching a person's teeth comprising obtaining a dental bleaching device according to claim 1 and placing it over at least a portion of the person's teeth for a desired time period.

27. A dental bleaching device, comprising:
a dental tray having flexibility so as to readily conform to a person's teeth during use;
a dental bleaching gel, positioned relative to said dental tray so as to contact a person's teeth during use, comprising at least one dental bleaching agent, at least one thickening agent, and a liquid or gel carrier; and
a protective adhesive composition, positioned relative to said dental tray so as to shield a person's soft tissues from said bleaching gel during use, comprising at least one tissue adhesion agent that includes at least one hydrophilic polymer, and said dental bleaching agent in a lower concentration than the dental bleaching agent contained in said dental bleaching gel.

28. A dental bleaching device as defined in claim 27, said dental tray comprising a barrier layer material that is sufficiently thin and flexible so as to be unable to maintain its shape as a dental tray absent external support, the dental bleaching device further comprising a removable exoskeleton that maintains said barrier layer material in the shape of said dental tray prior to use.

29. A dental bleaching device as defined in claim 27, said dental bleaching gel being sticky and viscous.

30. A dental bleaching device as defined in claim 27, said protective adhesive composition comprising a sticky and viscous gel.

31. A dental bleaching device as defined in claim 27, said protective adhesive composition being substantially solid prior to use and becoming more adhesive to teeth or gums when moistened with saliva or water.

32. A dental bleaching device, comprising:
a barrier layer in the form of a strip or patch having a flexibility so as to readily conform to a person's teeth during use;
a dental bleaching gel, positioned relative to said barrier layer so as to contact a person's teeth during use, comprising at least one dental bleaching agent, at least one thickening agent, and a liquid or gel carrier; and
a protective adhesive composition, positioned relative to said barrier layer so as to shield a person's soft tissues from said bleaching gel during use, comprising at least one tissue adhesion agent that includes at least one hydrophilic polymer, and said dental bleaching agent in a lower concentration than the dental bleaching agent contained in said dental bleaching gel.

33. A dental bleaching device as defined in claim 32, said dental bleaching gel being sticky and viscous.

34. A dental bleaching device as defined in claim 32, said protective adhesive composition comprising a sticky and viscous gel.

35. A dental bleaching device as defined in claim 32, said protective adhesive composition being substantially solid prior to use and becoming more adhesive to teeth or gums when moistened with saliva or water.

* * * * *

UNITED STATES PATENT AND TRADEMARK OFFICE
CERTIFICATE OF CORRECTION

PATENT NO. : 7,192,280 B2  Page 1 of 1
APPLICATION NO. : 10/783750
DATED : March 20, 2007
INVENTOR(S) : Allred et al.

It is certified that error appears in the above-identified patent and that said Letters Patent is hereby corrected as shown below:

Drawings
Sheet 3, Fig. 4, change the reference "10" to --40--

Column 19
Line 50, change "Incorporation" to --Incorporating--

Column 24
Example 5, change the percent composition of Glycerin from "73%" to --2%--

Column 33
Line 44, change "so at to" to --so as to--

Signed and Sealed this

Twenty-ninth Day of July, 2008

JON W. DUDAS
*Director of the United States Patent and Trademark Office*